US012760280B2

(12) United States Patent
Takebe et al.

(10) Patent No.: US 12,760,280 B2
(45) Date of Patent: Oct. 13, 2026

(54) FORMATION OF THREE-DIMENSIONAL ORGAN FROM PLURIPOTENT STEM CELLS, METHOD FOR GENERATING CELL CONDENSATE FOR SELF-ORGANIZATION

(71) Applicant: Public University Corporation Yokohama City University, Yokohama (JP)

(72) Inventors: Takanori Takebe, Yokohama (JP); Hideki Taniguchi, Yokohama (JP); Hiroshi Yoshikawa, Saitama (JP)

(73) Assignee: Public University Corporation Yokohama City University, Yokohama (JP)

( * ) Notice: Subject to any disclaimer, the term of this patent is extended or adjusted under 35 U.S.C. 154(b) by 0 days.

(21) Appl. No.: 18/745,880

(22) Filed: Jun. 17, 2024

(65) Prior Publication Data

US 2024/0336898 A1 Oct. 10, 2024

Related U.S. Application Data

(63) Continuation-in-part of application No. 16/768,019, filed as application No. PCT/JP2018/044144 on Nov. 30, 2018, now Pat. No. 12,012,616, application No. 18/745,880 is a continuation-in-part of application No. 15/121,934, filed as application No. PCT/JP2015/055695 on Feb. 26, 2015, now abandoned.

(30) Foreign Application Priority Data

Feb. 27, 2014 (JP) ................................ 2014-037341
Nov. 30, 2017 (JP) ................................ 2017-230647

(51) Int. Cl.

| | |
|---|---|
| ***C12N 5/071*** | (2010.01) |
| ***A61L 27/36*** | (2006.01) |
| ***C12N 5/074*** | (2010.01) |
| *A61K 35/51* | (2015.01) |
| *A61P 1/16* | (2006.01) |
| *G01N 33/50* | (2006.01) |

(52) U.S. Cl.

CPC ........ *C12N 5/0697* (2013.01); *A61L 27/3625* (2013.01); *A61L 27/3641* (2013.01); *C12N 5/0607* (2013.01); *A61L 2430/28* (2013.01); *C12N 2502/1358* (2013.01); *C12N 2502/28* (2013.01); *C12N 2506/03* (2013.01)

(58) Field of Classification Search

CPC ............................ C12N 5/0697; C12N 5/0607
See application file for complete search history.

(56) References Cited

U.S. PATENT DOCUMENTS

2013/0252337 A1* 9/2013 Yang ...................... C12M 23/12 435/395
2014/0289877 A1* 9/2014 Taniguchi ........... A61L 27/3804 435/1.1
2017/0067014 A1* 3/2017 Takebe .................... A61L 27/52

FOREIGN PATENT DOCUMENTS

WO WO-2015129822 A1 * 9/2015 ......... A61L 27/3886

OTHER PUBLICATIONS

Cook et al., (2012) Micromarrows—Three dimensional coculture of hematopoietic stem cells and mesenchymal stromal cells. Tissue Engineering Part C: Methods, 18(5): pp. 391-396 (Year: 2012).*
Napolitano et al., (2007) Scaffold-free three-dimensional cell culture utilizing micromolded nonadhesive hydrogels. BioTechniques, 43(7):pp. 494-500 (Year: 2007).*
Generating size-controlled spheroids and embryoid bodies using AggreWellTM microwell plates. Datasheet [online] StemCell Technologies, 2026 [retrieved on Feb. 19, 2026]. Retrieved from the Internet: (Year: 2026).*
Ye et al., (2012) Promise and challenges of human iPSC-based hematologic disease modeling and treatment. International Journal of Hematology. 95: 601-609 (Year: 2012).*
Takebe et al., (2014) Generation of a vascularized and functional liver from an iPSC-derived organ bud transplant. Nature Protocols , 9: pp. 396-409 (Year: 2014).*
Rettinger et al., (2014) In vitro characterization of scaffold-free three-dimensional stem cell aggregates. Cell and Tissue Research, 358: 395-405 (Year: 2014).*

* cited by examiner

*Primary Examiner* — Kara D Johnson
(74) *Attorney, Agent, or Firm* — Morgan, Lewis & Bockius LLP

(57) ABSTRACT

The present disclosure relates to construction of three-dimensional organs from pluripotent stem cells. The present disclosure also relates to a method of forming a cell condensate for self-organization.

18 Claims, 22 Drawing Sheets

Lung

A

B

GL; glomerulus; PT, proximal tubule; P, podocyte; E, capillary endothelium; R, red blood cell; M, mesangial cell; bm, basement membrane; fp, interdigitating foot processes; mv, microvilli; ly, lysosome; mt, mitochondria WT1 (Wilms' tumor suppressor-1)
LTA (lectin Lotus tetragonobulus agglutinin)

FORMATION OF THREE-DIMENSIONAL ORGAN FROM PLURIPOTENT STEM CELLS, METHOD FOR GENERATING CELL CONDENSATE FOR SELF-ORGANIZATION

TECHNICAL FIELD

The present disclosure relates to construction of three-dimensional organs from pluripotent stem cells. The present disclosure also relates to a method of forming a cell condensate for self-organization.

BACKGROUND ART

The preset inventors have developed a method of preparing three-dimensional tissues (organ primordia) by mixing functional cells used in regenerative medicine, etc. (such as pluripotent stem cell-derived organ cells) with umbilical cord-derived vascular endothelial cells and bone marrow-derived mesenchymal cells; and reported that organ primordia prepared by this method are superior to those cells obtained by directed differentiation under plane culture, in terms of function in vitro and therapeutic effects for disease model animals.

Recently, methods using the self-organization capacity of cells which they inherently possess have been attracting attention as methods of forming tissues/organs with complex structures. Self-organization is a process in which one or a few elements construct complex higher structures by exerting intrinsic properties of their own without receiving specific "instructions" (information) from the outside. For example, natural phenomena in which spontaneous order arises from patternless aggregates to form patterns, as in crystallization of snow, are observed. Self-organization is also used in the field of engineering, e.g. in nanotechnology or in preparing optical crystals.

For inducing self-organization, it is necessary to form an aggregate consisting of homogeneous cells in a high-density environment. Studies have been reported in which aggregates were prepared from cultured ES/iPS cells to generate brain, optic cup, pituitary gland, teeth, etc. As a technique for preparing such aggregates, a method is mainly used in which tissues of several hundred μm level are formed from cell aggregates of a small number of cells (about several thousand) by using a substrate such as a 96-well plate with U- or V-shaped bottoms that permits cells to gather in the bottom. However, it has been difficult to achieve formation of larger size (200 μm or more) cell condensates from a large number of cells (several ten thousand to several million cells). Therefore, it has been difficult to apply conventional methods to preparation of cell aggregates consisting of diverse cells.

Under these circumstances, it has been desired to develop a self-organization based technique for preparing cell condensates for generating large and complex tissues/organs (as from humans) compared to tissues/organs of small animals like mouse.

PROBLEM FOR SOLUTION

Conventional methods using two types of cells, one derived from umbilical cord and the other from bone marrow, have the following problems which are ultimate challenges for practical application: (1) the quality of resultant organ primordia varies greatly depending on donors; (2) the growth capacities of cell sources are limited; and (3) it is difficult to secure immunocompatibility because cells are derived from different sources. Moreover, since umbilical cord/bone marrow-derived cells are highly matured cells, they greatly differ in differentiation stage from the immature cells required for generation of organ primordia, and largely depart from the scenario of in vivo development.

In another aspect, for the development of drugs or realization of regenerative medicine for diseases in kidney, liver, lung, etc., it is essential to recapitulate three-dimensional complex structures (integrating not only a vasculature but also higher structures such as ureteral structure, biliary structure, tracheal structure, etc.) and cell polarity. Moreover, induction of an organ of interest is achieved through interactions with other organs. Therefore, in order to maximize the function of tissues induced from pluripotent stem cells or tissues isolated from individuals, three-dimensional tissue constructs should be formed which enable reconstitution of continuity with diverse higher structures and other organs. According to conventionally devised methods, however, only tissue constructs having a vascular structure alone have been prepared from the three types of cells or tissues. No technique has been invented for preparing more complex, higher structures (such as ureteral structure, biliary structure and tracheal structure). It is one object of the present invention to find out the requirements necessary for preparing a cell condensate in vitro from a large number of cells (several ten thousand to several million cells). It is another object of the present invention to provide a method of forming a cell condensate for self-organization which is capable of realizing complex higher structures (such as liver and kidney) and interactions with other organs.

MEANS TO SOLVE THE PROBLEM

The present inventors have succeeded in preparing organ primordia from differentiation stage-synchronized multiple immature cells by ensuring that all three cell species used to prepare three-dimensional organ primordia are made from induced pluripotent stem cells (iPS cells). Specifically, the present inventors have prepared human liver buds using a combination of iPS cell-derived hepatic endoderm cells, iPS cell-derived vascular endothelial cells and iPS cell-derived mesenchymal cells, and compared them with those human liver buds which are prepared by conventional methods using a combination of iPS cell-derived hepatic endoderm cells, umbilical cord-derived vascular endothelial cells and bone marrow-derived mesenchymal cells, in terms of in vitro albumin secretion capacity, gene expression of differentiation markers, and so on. As a result, a remarkable improvement of function was recognized compared with the liver buds prepared by conventional methods. Further, when liver buds equivalent to $6\times10^6$ iPS cell-derived hepatic endoderm cells were transplanted into immunodeficient animal (NOD/scid mouse), the same result was obtained from the human albumin level secreted into the serum. According to the present disclosure, it becomes possible to achieve a remarkable improvement of function and also to reduce cost and labor required for quality evaluation and production. It is highly probable that similar effects will be obtained by replacing iPS cells with other pluripotent stem cells (e.g., embryonic stem (ES) cells).

A summary of the present disclosure is as described below.

(1) An organ bud prepared from vascular cells, mesenchymal cells and tissue or organ cells, wherein each of the vascular cell, the mesenchymal cell and the tissue or organ cell has been induced from pluripotent stem cells.

(2) The organ bud of (1) above, which is a structure capable of differentiating into an organ through maturing.

(3) The organ bud of (1) or (2) above, wherein the pluripotent stem cell is derived from human.

(4) The organ bud of any one of (1) to (3) above, wherein the pluripotent stem cell is at least one cell selected from the group consisting of induced pluripotent stem cell and embryonic stem cell.

(5) The organ bud of any one of (1) to (4) above, wherein the organ cell is hepatocyte and the organ bud is liver bud.

(6) The organ bud of (5) above, wherein the hepatocyte is TBX3 positive and ADRA1B positive.

(7) The organ bud of any one of (1) to (6) above, wherein the mesenchymal cell is CD166 positive and CD31 negative.

(8) The organ bud of any one of (1) to (7) above, wherein the mesenchymal cell is LHX2 positive and WT1 positive.

(9) The organ bud of (8) above, wherein the transcriptions of FOXF1, HLX1, COL4A and ALCAM of the mesenchymal cell are activated and the mesenchymal cell is LHX2 positive, WT1 positive and MIIA positive.

(10) The organ bud of any one of (1) to (9) above, wherein the vascular cell is CD31 positive and CD144 positive.

(11) The organ bud of (10) above, wherein expression of at least one gene selected from the group consisting of PECAM1, CDH5, KDR and CD34 of the vascular cell is increased relative to the corresponding expression in the pluripotent stem cell before directed differentiation.

(12) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and b) culturing the resultant cells from the above step in the presence of an FGF and a factor belonging to the TGF-β superfamily for directed differentiation into TBX3 and ADRA1B co-positive cells.

(13) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(14) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(15) The organ bud of any one of (1) to (12) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(16) The organ bud of any one of (1) to (15) above, wherein LHX2 and WT1 co-positive cells obtained through the following steps are used as mesenchymal cells:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(17) The organ bud of any one of (1) to (15) above, wherein CD166 positive but CD31 negative cells obtained through the following steps are used as mesenchymal cell-:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(18) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(19) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-β type I receptor.

(20) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(21) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

(22) A method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

(23) The method of (22) above, wherein the cells are cultured without using scaffold materials.

(24) A method of preparing a tissue or an organ, comprising transplanting the organ bud of any one of (1) to (21) above into a non-human animal and differentiating the organ bud into a tissue or an organ.

(25) A method of transplanting an organ bud, comprising transplanting the organ bud of any one of (1) to (21) above into a human or a non-human animal.

(26) A method of regeneration or function recovery of a tissue or an organ, comprising transplanting the organ bud of any one of (1) to (21) above into a human or a non-human animal and differentiating the organ bud into a tissue or an organ.

(27) A method of preparing a non-human chimeric animal, comprising transplanting the organ bud of any one of (1) to (21) above into a non-human animal and differentiating the organ bud into a tissue or an organ.

(28) A method of evaluating a drug, comprising using at least one member selected from the group consisting of the organ bud of any one of (1) to (21) above, the tissue or organ prepared by the method of (24) above and the non-human chimeric animal prepared by the method of (27) above.

(29) A method of preparing TBX3 and ADRA1B co-positive cells, comprising:

a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and b) culturing the resultant cells from the above step in the presence of an FGF and a factor belonging to the TGF-β superfamily for directed differentiation into TBX3 and ADRA1B co-positive cells.

(30) A method of preparing TBX3 and ADRA1B co-positive cells, comprising:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(31) A method of preparing TBX3 and ADRA1B co-positive cells, comprising:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(32) A method of preparing TBX3 and ADRA1B co-positive cells, comprising:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(33) A method of preparing LHX2 and WT1 co-positive cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(34) A method of preparing CD166 positive but CD31 negative cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(35) A method of preparing CD31 and CD144 co-positive cells, comprising:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(36) A method of preparing CD31 and CD144 co-positive cells, comprising:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-β type I receptor.

(37) A method of preparing CD31 and CD144 co-positive cells, comprising:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(38) A method of preparing CD31 and CD144 co-positive cells, comprising:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

In another aspect, the present inventors have succeeded in preparing three-dimensional tissues/organs having complex higher structures from isolated, multiple types of cells or tissues by the operations 1 to 4 described below. Thus, the present invention has been achieved.

1. Preparation of Necessary Cells/Tissues

A) Cells/tissues of a desired type or types that are necessary for self-organization into tissues with complex structures are prepared. The types or numbers to be combined do not matter.

B) A mixture in solution that consists of a desired type or types of cells/tissues in a total number of approximately 2 million is mixed with approximately 100,000 to 400,000 isolated mesenchymal cells.

2. Preparation of Support

A) A support with an appropriate stiffness is formed and solidified on a cell culture dish. Preferable materials for the support include, but are not limited to, hydrogels (such as polyacrylamide gel).

B) Chemical/physical modifications are provided on the prepared support. Giving such modifications, however, is not an essential requirement. Preferable chemical factors include, but are not limited to, Matrigel and laminin C) The stiffness of the support need not be uniform and may vary depending on the shape, size and quantity of an condensate of interest. The stiffness of the support may be provided with aspatial/temporal gradient or patterned, for use in subsequent experiments.

3. Preparation and Culture of Cell Condensates

A) The cell/tissue mixture in solution as prepared in 1 above is plated on the support prepared in 2 above to form condensates. The thus formed condensates may be cultured for an elongated period so that it can be used for self-organization into organs of interest in vitro.

By combining mesenchymal cells with a culture substrate that permets cells to gather in the bottom, condensates can also be prepared from the cells if they are small in number.

4. Transplantation of Cell Condensates

By subjecting the condensates prepared in 3 above to long-term culture or transplanting them into living bodies to induce blood perfusion and allow self-organization into higher tissues with a complex structure, tissues/organs can be prepared that have a highly ordered tissue structure comparable to that of adult tissues.

The above-described technique which prepares a complex cell condensate consisting of cells of a desired type or types by combining mesenchymal cells with physicochemical properties of a support has not existed to date and is believed to provide a method that is extremely high in novelty.

The gist of the present disclosure according to some embodiments is as described below.

(1) A method of preparing a cell condensate in vitro, comprising culturing a mixture of cells and/or tissues of a desired type and mesenchymal cells to form a cell condensate.

(2) The method of (1) above, wherein the cell condensate is capable of forming a three-dimensional tissue structure that has been provided with higher structures by self-organization.

(3) The method of (1) or (2) above, wherein the mixture of cells and/or tissues of a desired type and mesenchymal cells is cultured on a gel-like support on which the mesenchymal cell is capable of contraction.

(4) The method of (3) above, wherein the culture is two-dimensional culture.

(5) The method of (3) or (4) above, wherein the gel-like support is planar or the side of the gel-like support on which culture is performed has a U- or V-shaped cross-section.

(6) The method of any one of (3) to (5) above, wherein the stiffness of the central part of the gel-like support is greater than the stiffness of the peripheral part thereof.

(7) The method of any one of (3) to (5) above, wherein the stiffness of the peripheral part of the gel-like support is greater than the stiffness of the central part thereof.

(8) The method of any one of (3) to (5) above, wherein the gel-like support is patterned and has one or more patterns in which the stiffness of the central part is greater than the stiffness of the peripheral part.

(9) The method of any one of (3) to (5) above, wherein the gel-like support is patterned and has one or more patterns in which the stiffness of the peripheral part is greater than the stiffness of the central part.

(10) The method of any one of (1) to (9) above, wherein the cells and/or tissues of a desired type have a total cell count of 400,000 or more and the mesenchymal cells are 100,000 to 400,000 in number.

(11) The method of any one of (1) to (10) above, wherein the size of the cell condensate is 1 mm or more.

(12) The method of any one of (1) to (11) above, wherein the cell condensate is formed autonomously.

(13) The method of any one of (1) to (12) above, wherein the mixture of cells and/or tissues of a desired type and mesenchymal cells is cultured without using scaffold materials.

(14) The method of any one of (1) to (13) above, wherein the cells and/or tissues mixed with the mesenchymal cells are derived from liver, pancreas, intestine, lung, kidney, heart, brain or cancer.

(15) The method of any one of (1) to (13) above, wherein the cells mixed with the mesenchymal cells are pluripotent cells.

(16) The method of any one of (1) to (13) above, wherein the tissues mixed with the mesenchymal cells are tissues induced from pluripotent cells.

(17) The method of (15) or (16) above, wherein the pluripotent cell is a pluripotent cell obtained from a living body, a pluripotent cell obtained by induction from reprogramming or a mixture thereof.

(18) A cell condensate prepared by the method of any one of (1) to (17) above.

(19) A method of preparing a three-dimensional tissue structure, comprising allowing self-organization of a cell condensate prepared by the method of any one of (1) to (17) above to form a three-dimensional tissue structure that has been provided with higher structures.

(20) A gel-like culture support wherein the side on which culture is performed has a U- or V-shaped cross-section.

(21) A gel-like culture support wherein the stiffness of the central part thereof is greater than the stiffness of the peripheral part thereof.

(22) A gel-like culture support wherein the stiffness of the peripheral part thereof is greater than the stiffness of the central part thereof.

(23) A gel-like support having one or more patterns in which the stiffness of the central part is greater than the stiffness of the peripheral part.

(24) A gel-like support having one or more patterns in which the stiffness of the peripheral part is greater than the stiffness of the central part.

(25) A method of preparing a cell condensate in vitro, comprising culturing a mixture of cells and/or tissues of a desired type and mesenchymal cells on the gel-like culture support of any one of (20) to (24) above to thereby form a cell condensate.

EFFECT OF THE INVENTION

The method of the present disclosure is advantageous over the conventional method using the two types of cells, one derived from umbilical cord and the other from bone marrow, in the following points: (1) the resultant organ primordia are stable in quality because of being non-donor dependent, (2) organ primordia generated from three types of cells that are entirely derived from iPS cells are dramatically superior to conventional ones in functionality and (3) it becomes easy to secure immunocompatibility.

According to another aspect of the present disclosure, a cell condensate of theoretically any complex composition can be formed by combining a mesenchymal stem cell and a support or a substrate that will allow cells to gather in the bottom. According to the present disclosure, tissues and organs can be constructed without using scaffolds.

First, the cell condensate of the present disclosure is expected to find use as an artificial constitution system for more complex tissues and organs. For example, with the cell condensate of the present disclosure, it may be possible to prepare three-dimensional complex structures that are provided with not only a vascular network but also higher structures such as ureteral structure, biliary structure, tracheal structure, etc. Further, a great number of organs essentially require that reconstitution associated with other organs be realized in order to exhibit their functions; e.g., in liver, reconstitution of junctions with bile duct and pancreatic duct and connection to duodenum is essential for exhibiting its function. According to the present disclosure, a cell condensate which recapitulates interactions with other organs is prepared. This cell condensate is expected to find use as a system for inducing self-organization into complex organs existing in the body.

Secondly, since the present disclosure uses an inexpensive and comparatively easy-to-process support, its industrial applicability toward mass production of tissues is high. Mass production of tissues of a desired shape, size and number can be realized at low cost by combining the cell condensate with the multi-patterning of the support or other techniques.

The technique of generating a 3D tissue construct self-organized from a cell condensate prepared from stem cells such as iPS cells is applicable to generation of human functional cells which has been difficult to achieve to date; transplantation of tissues and organs; screening in drug discovery; a novel analysis system for evaluating the relationships between development of drug effects and supporting tissues (blood vessels, nerves, stroma, etc.) and so on.

The present specification incorporates U.S. Patent Application Publication Nos. 2017/0067014 and 2020/0362315 and Japanese Patent Application Nos. 2014-037341 and 2017-230647 by reference in their entirety.

(B) Formation of self-organized, iPSC or iPS cell-derived liver buds (C) Temporal development of dynamics of cell condensate formation. (Red) square root of the projected area of condensate. This can be used as an indicator showing the location of the edge of condensate. After about 13 hr, an exponential function provides good approximation (black dotted line); (Blue) circularity of condensate calculated from the projected area and the contour line length of condensate.

(D) Necessity of mesenchymal cells in cell condensate formation (E) Inhibitory experiment against cell condensate formation process using various chemical substances.

(F) Time-dependent changes in the content of active form of myosin and the inhibition thereof.

Figure 2:
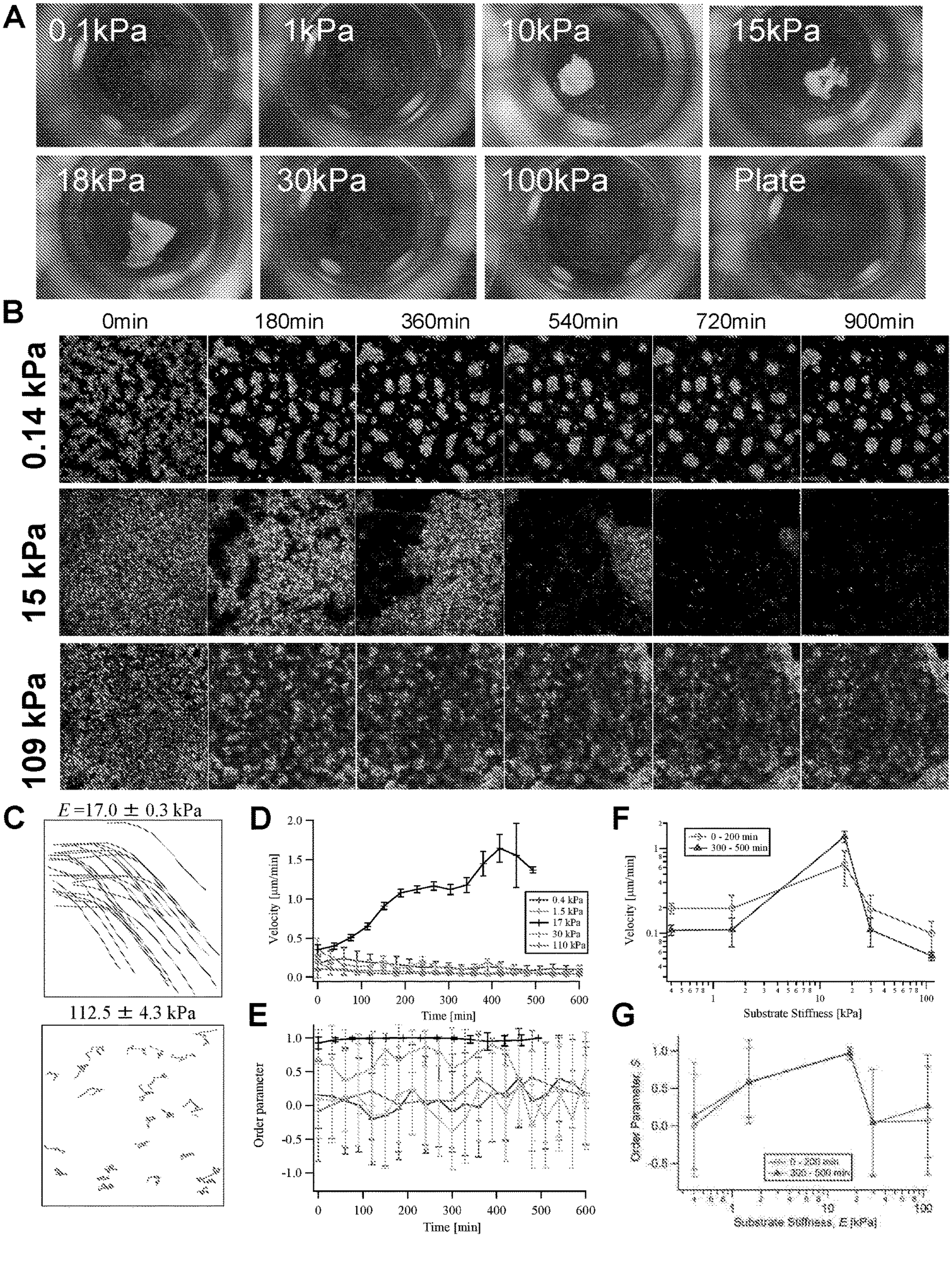

FIG. 2 Optimization of stiffness environment in cell condensate formation (A, B) Cell condensate formation experiments under various stiffness conditions. (A) Macroscopic observation after 48 hr of culture. (B) Time-dependent changes in cell movement under confocal laser microscope. (C-G) Characterization of MSCs in cell condensate. trajectories (C); time dependency of velocity and order parameter (D, E); and dependency on substrate stiffness (F, G).

Figure 3:
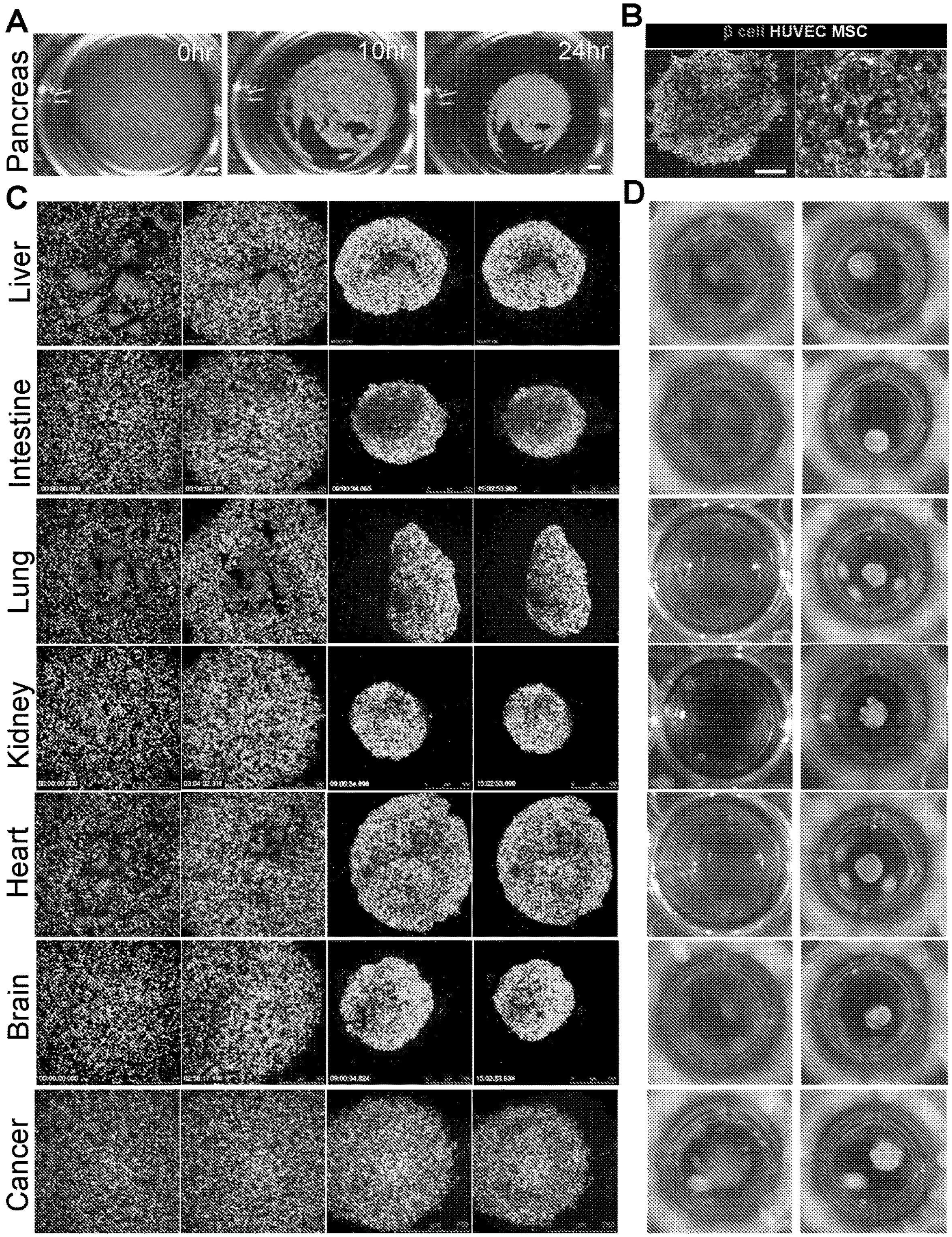

FIG. 3 Experiments on the formation of condensates for self-organization using diverse tissue-derived cells (A, B) Cell condensate formation using pancreatic β cells (A) and self-organization (B).

(C, D) Cell condensate formation experiments using other organ cells/tissues.

Figure 4:
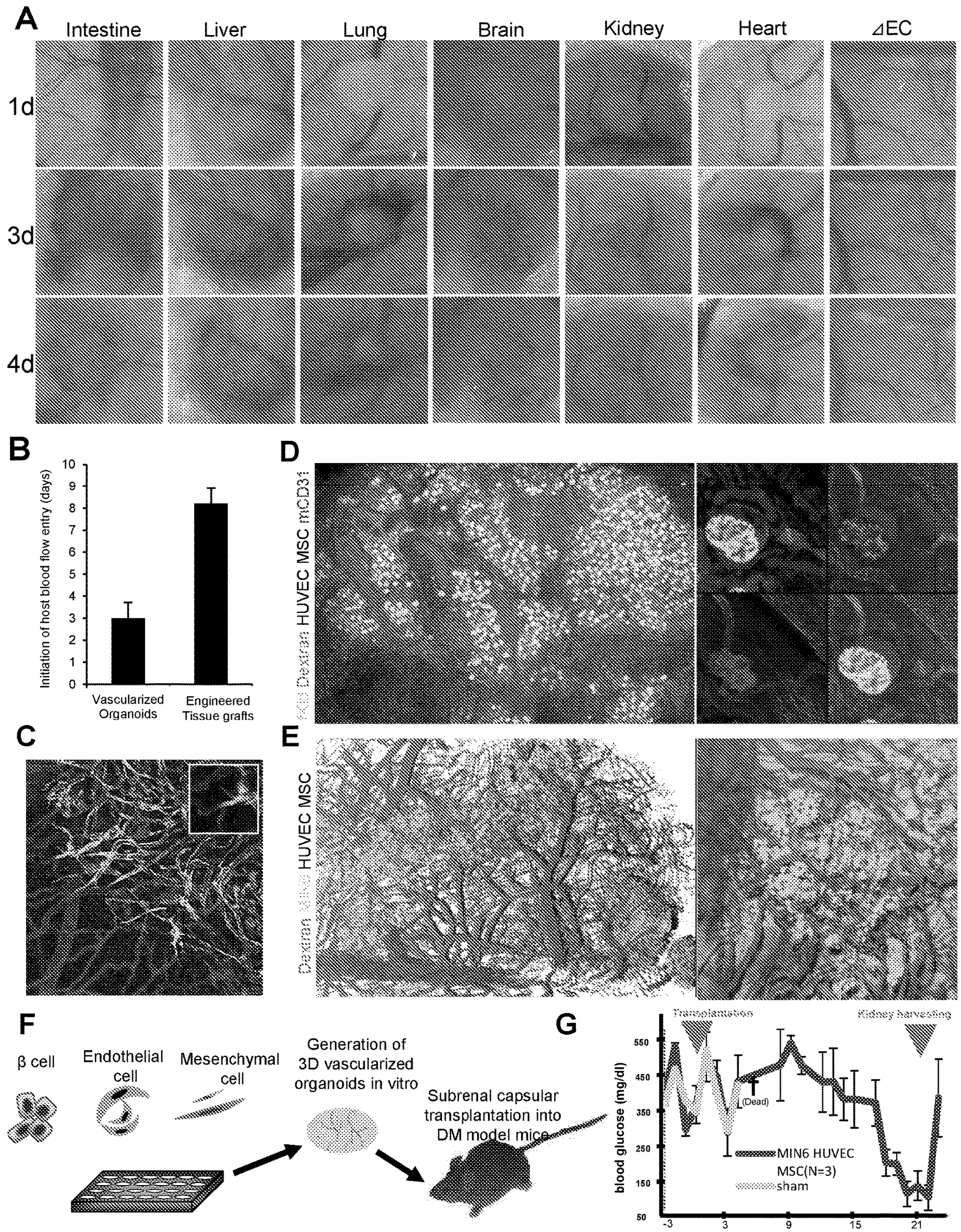

FIG. 4 In vivo self-organization of diverse tissue-derived cell condensates and development of their function (A) Functional vascularization occurs in 2 to 3 days after transplantation.

(B) Comparison between the conventional and invention methods of the time required for blood perfusion.

(C) Direct anastomosis of mouse and human blood vessels.

(D) Glomeruli and renal tubules formed by cell condensates prepared from embryonic renal cells.

(E) Islet-like tissues formed by cell condensates prepared from β cells.

(F) Model for evaluating the therapeutic effect of cell condensates prepared from β cells.

(G) Time-dependent changes in blood glucose level in diabetic model mice transplanted with cell condensates prepared from β cells.

Figure 5:
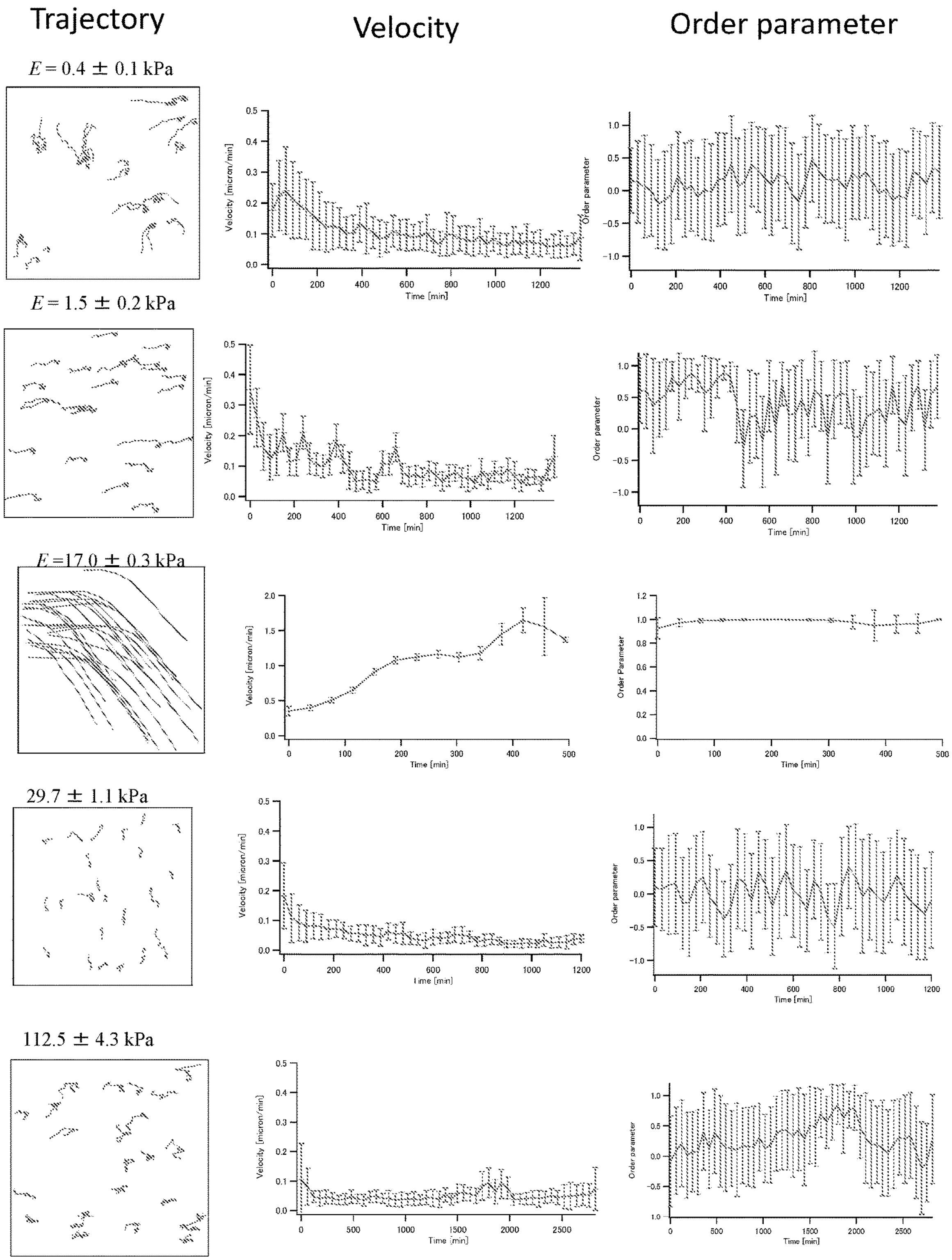
Figure 6:
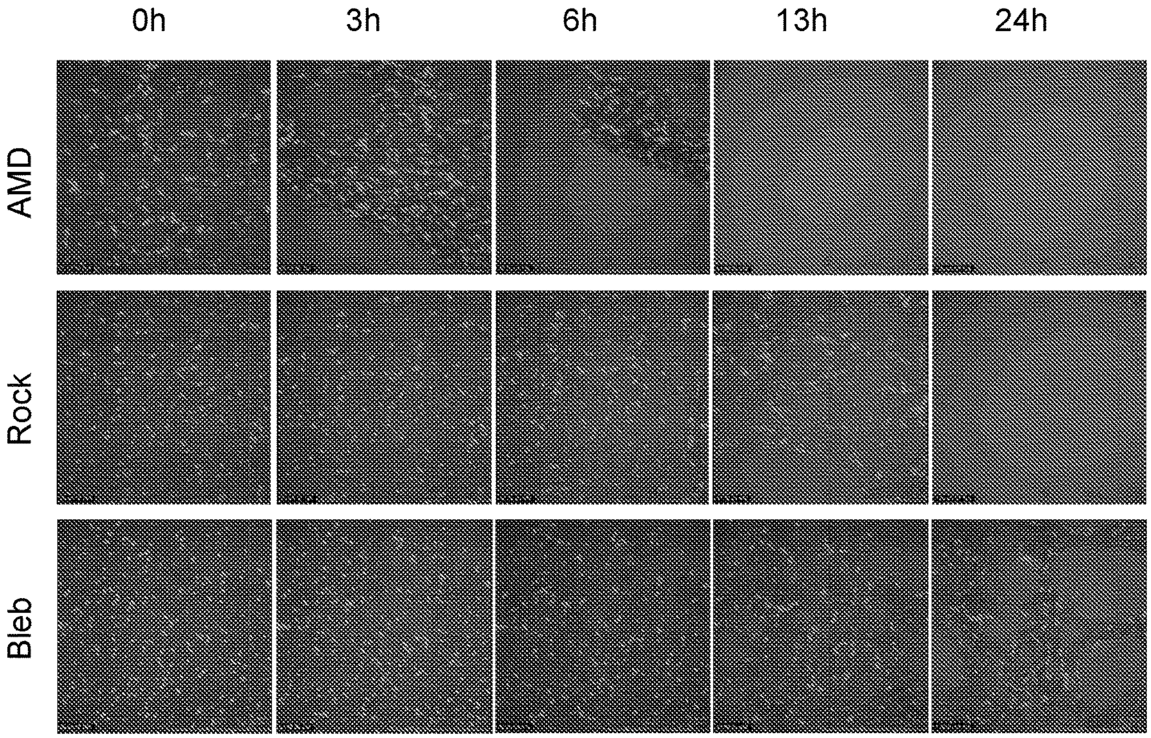

FIG. 5 Time-dependent changes in the trajectory, velocity and order parameter of MSCs in cell condensates under various stiffness conditions FIG. 6 Chronological observation of cell condensate formation processes using various inhibitors.

Figure 7:
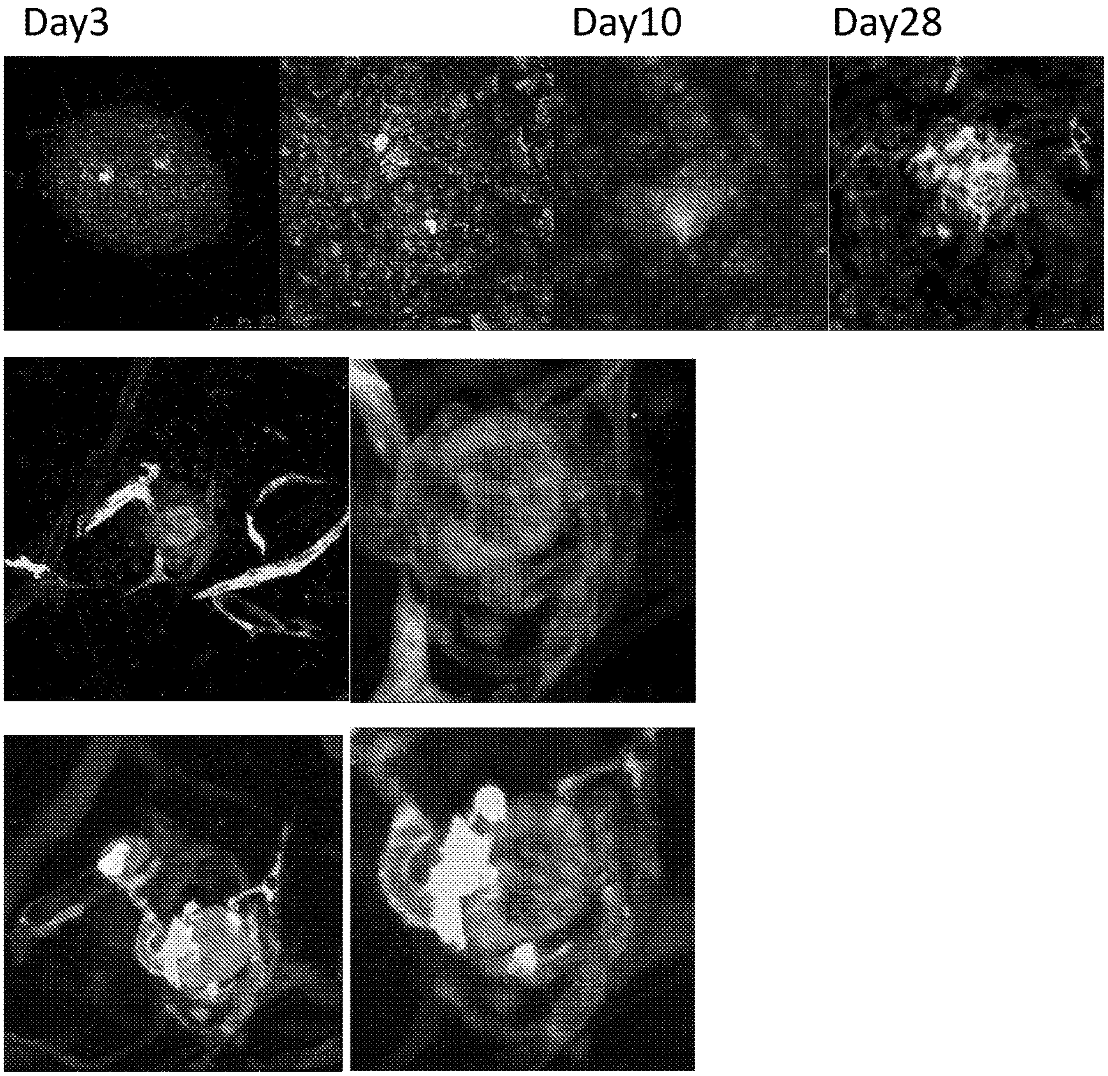

FIG. 7 In vivo self-organization of cell condensate using adult kidney tissue.

Figure 8:
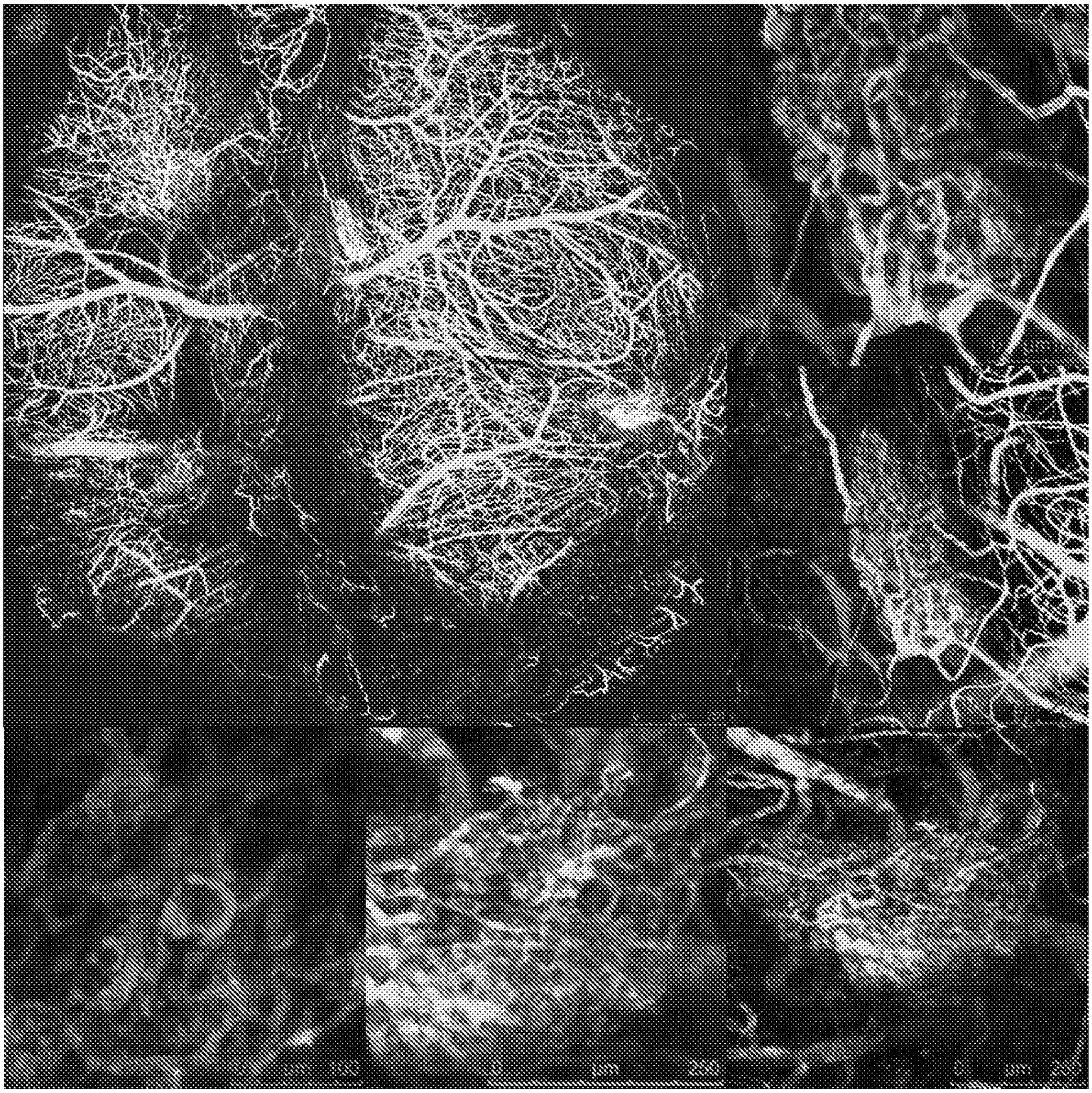

FIG. 8 In vivo self-organization of cell condensate using embryonic lung tissue.

Figure 9:
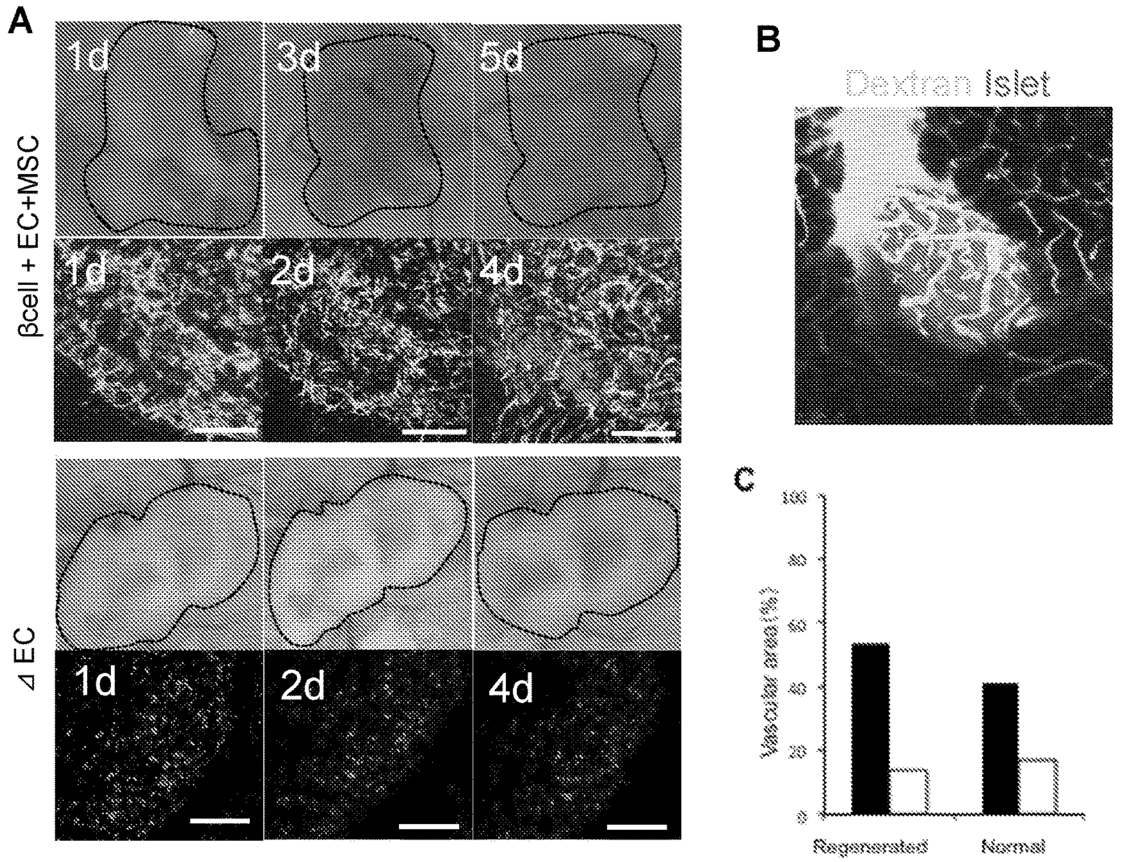

FIG. 9 Tracing of in vivo vascularization process in cell condensate using β cells.

Figure 10:
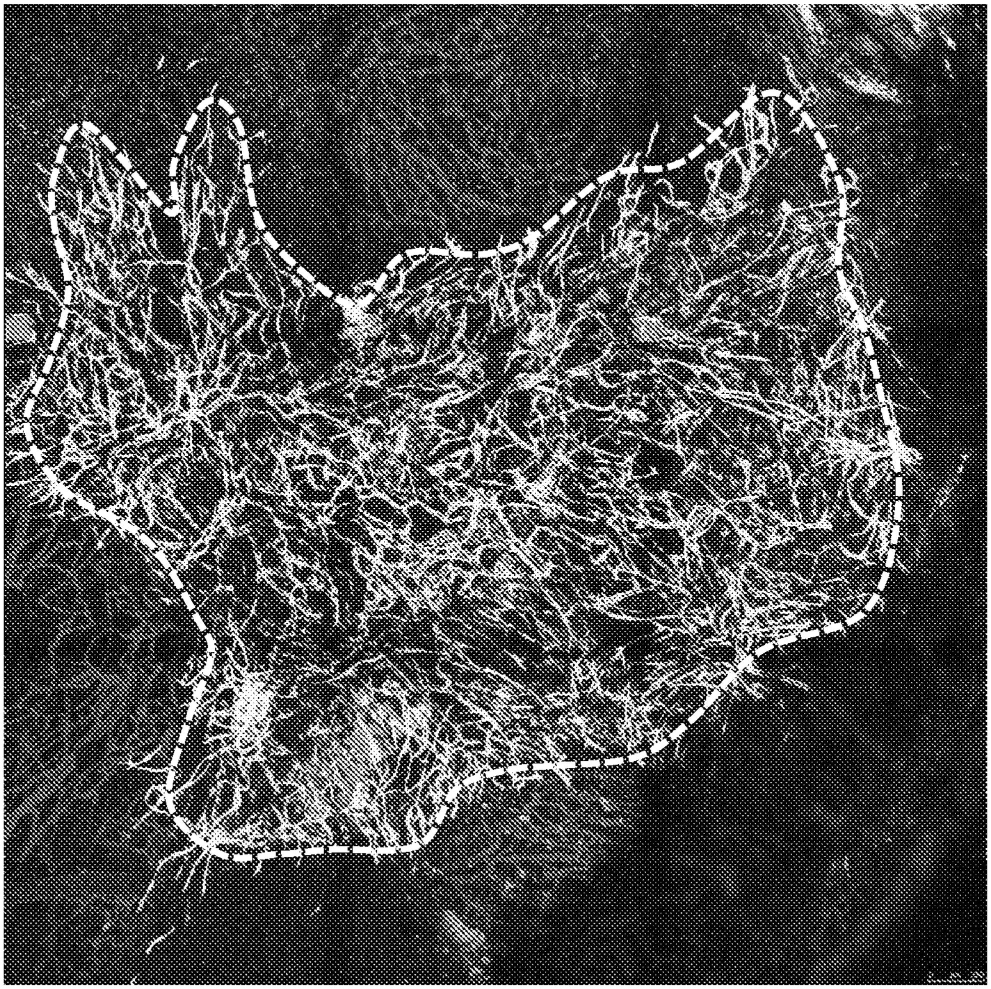

FIG. 10 Observation of in vivo junctions with host blood vessels in cell condensate using β cells.

Figure 11:
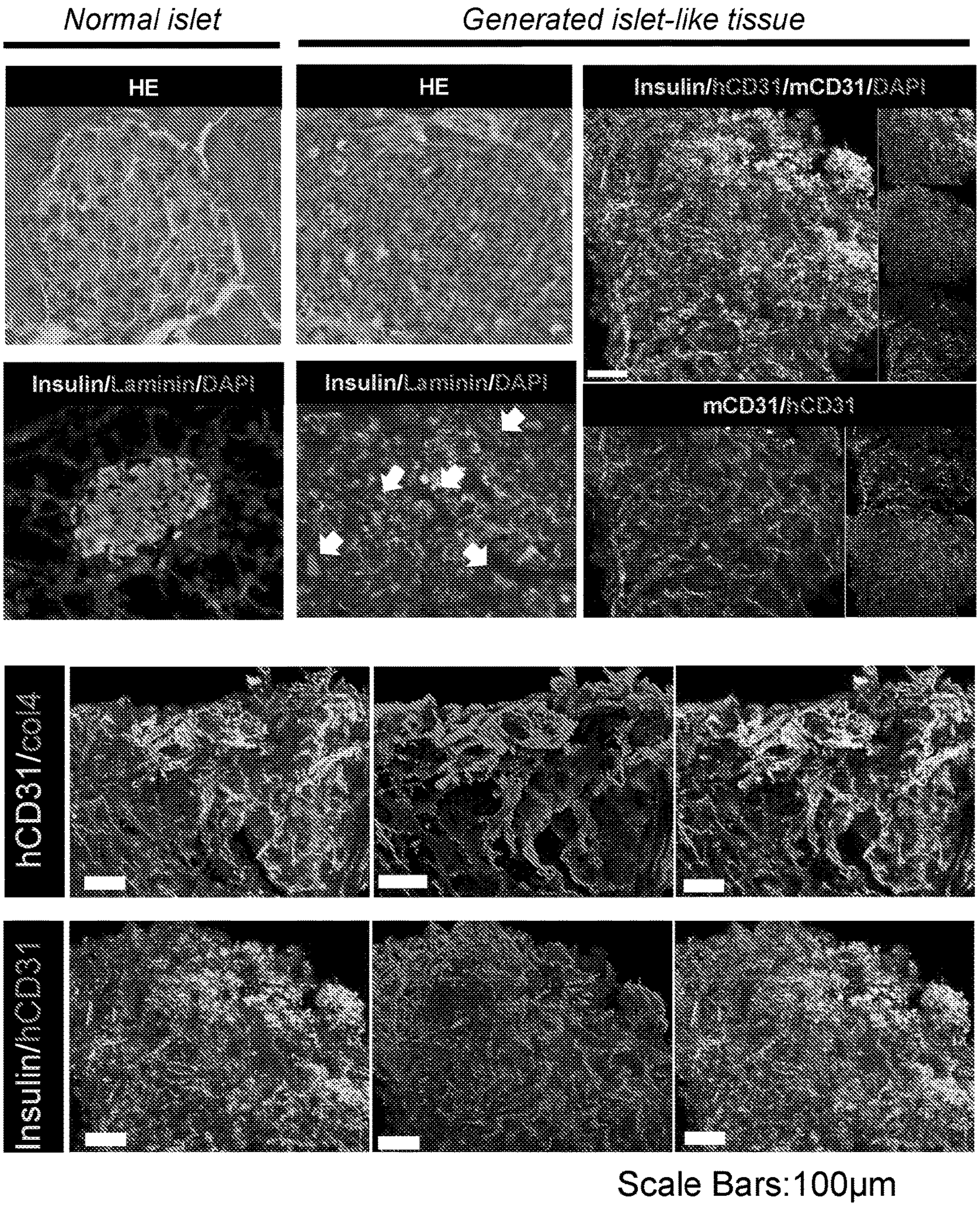

FIG. 11 Histological analysis of tissues generated from cell condensate using β cells.

Figure 12:
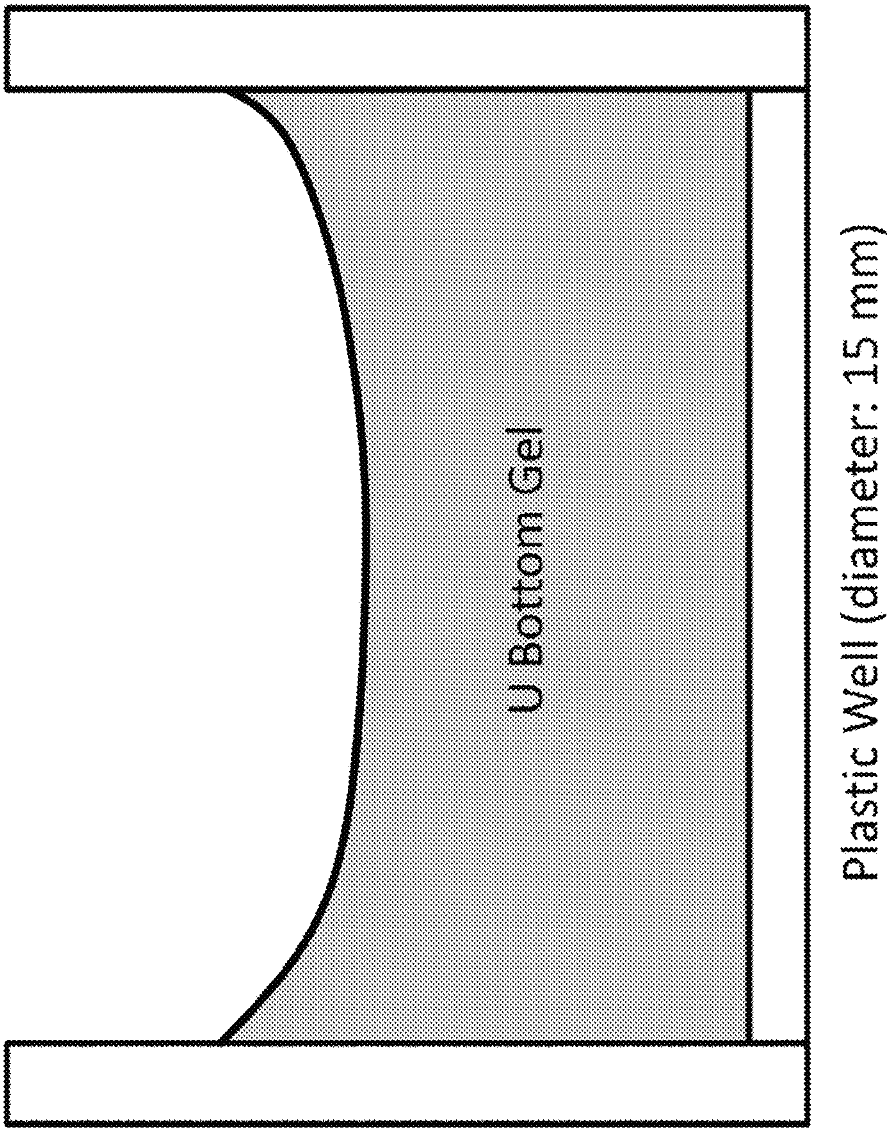

FIG. 12 Cross section of U-bottom gel.

Figure 13:
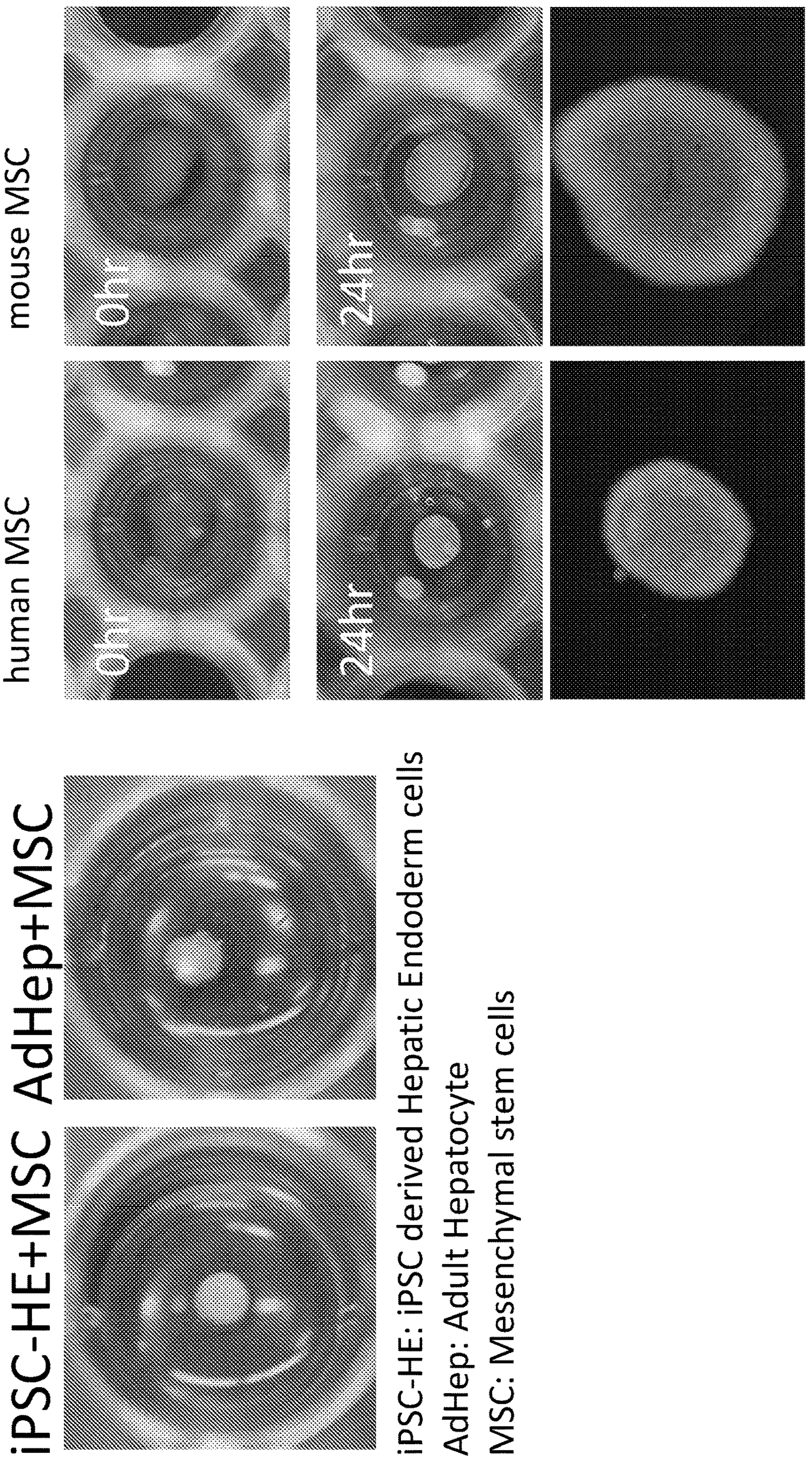

FIG. 13 (A) Formation of cell condensates containing no vascular endothelial cells. (B) Formation of cell condensates using human or mouse mesenchymal cells.

Figure 14:
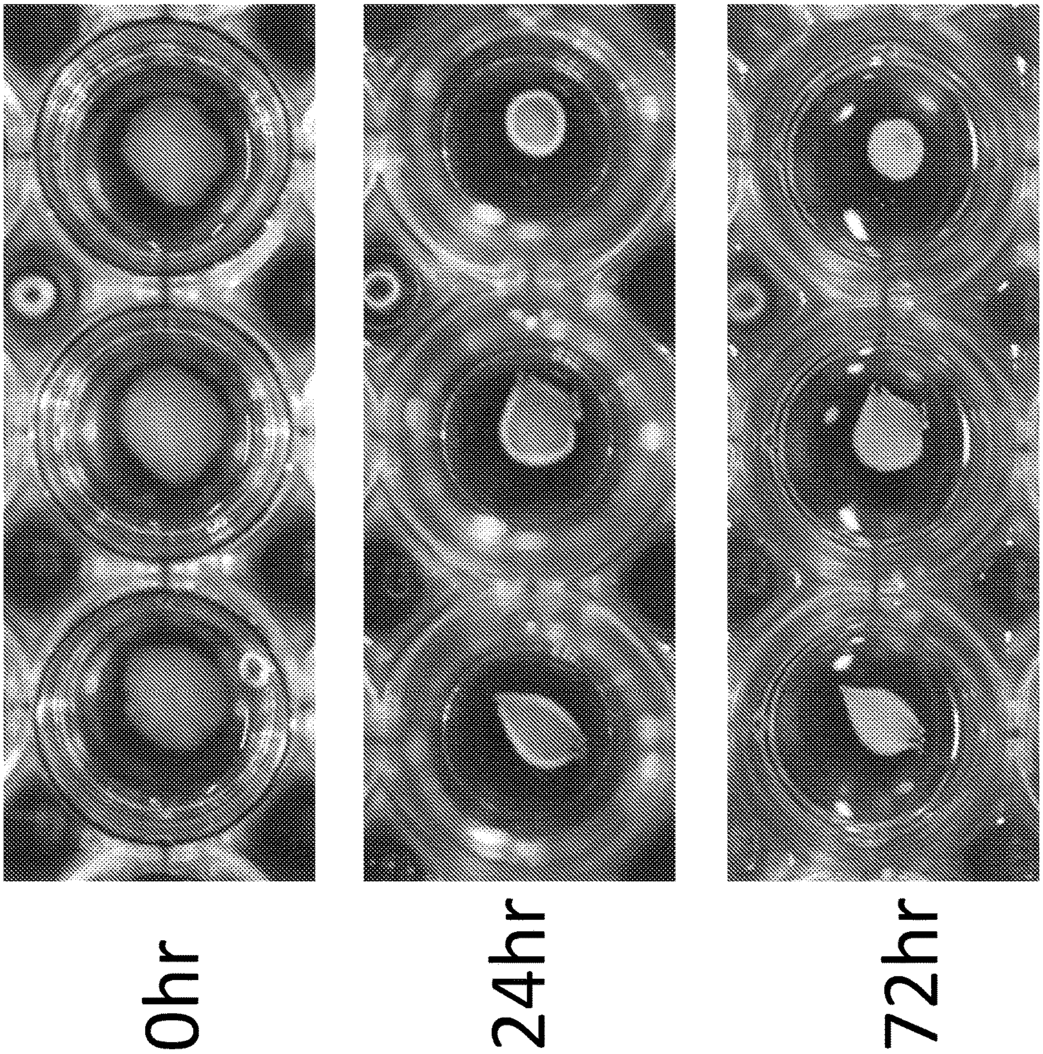

FIG. 14 Formation of cell condensates using U-bottom gel.

Figure 15:
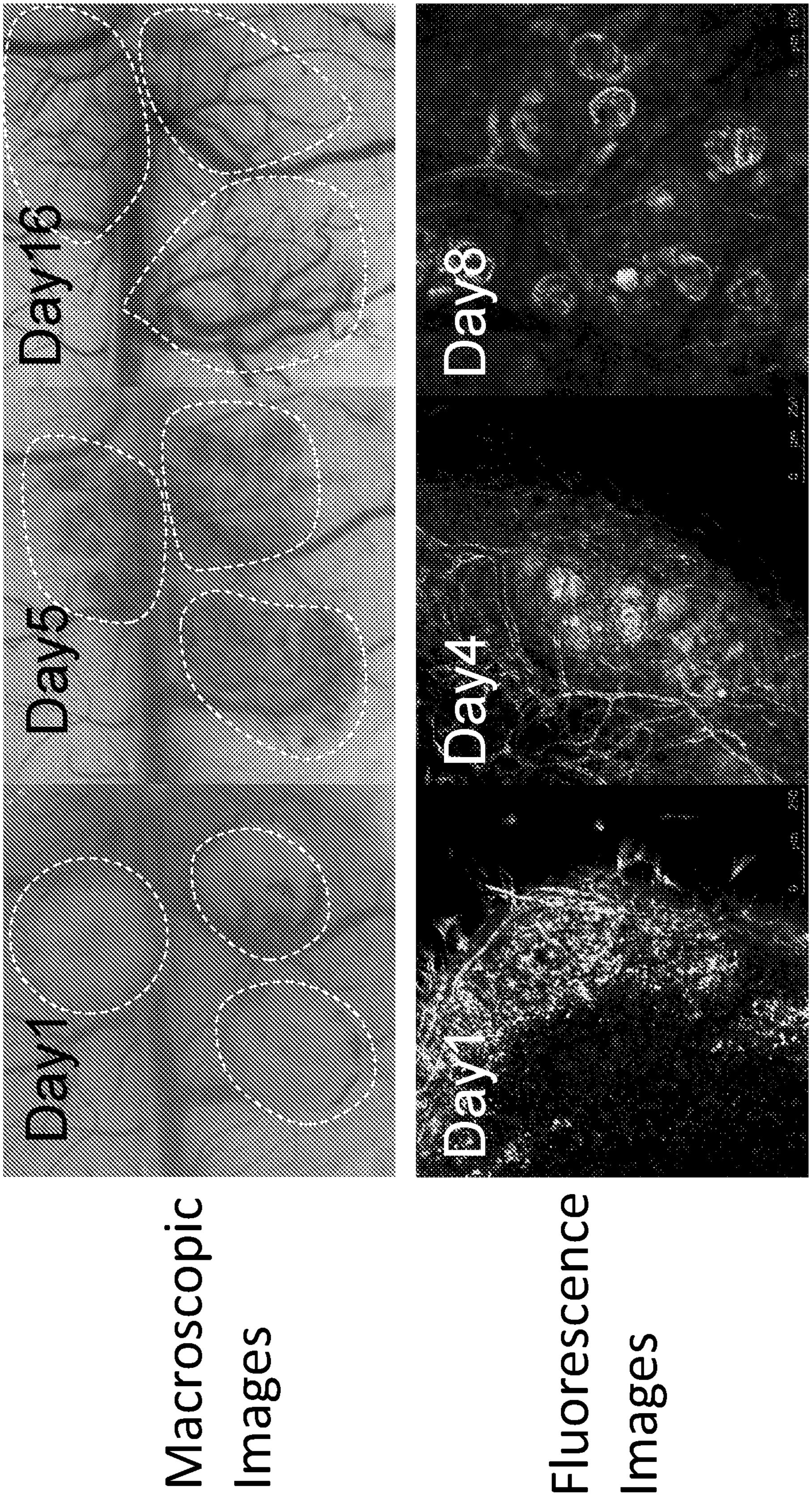

FIG. 15 Reconstitution of a functional vascular network by transplantation of a kidney primordium prepared on a support.

Figure 16:
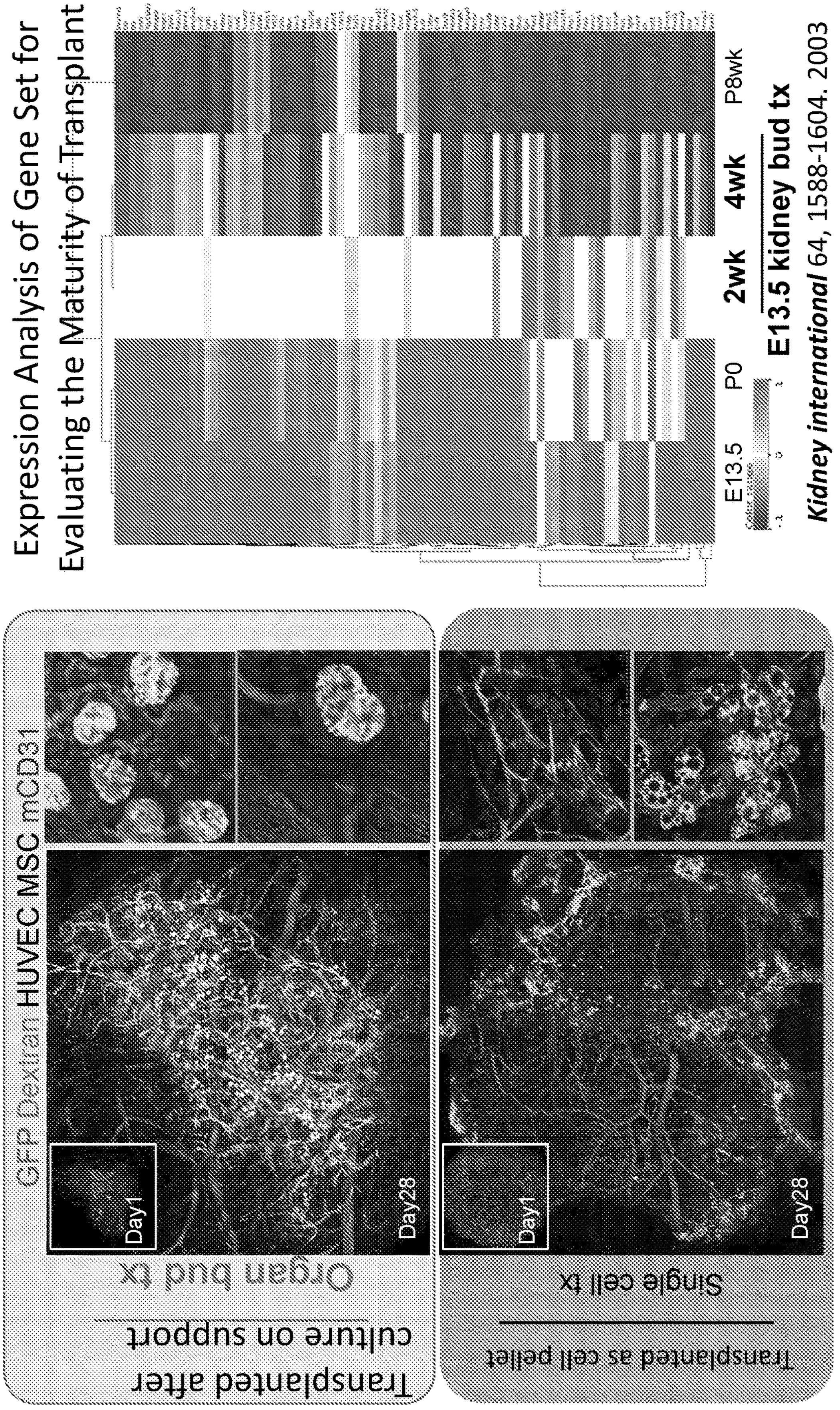

FIG. 16 Maturation of transplanted kidney primordium.

Figure 17:
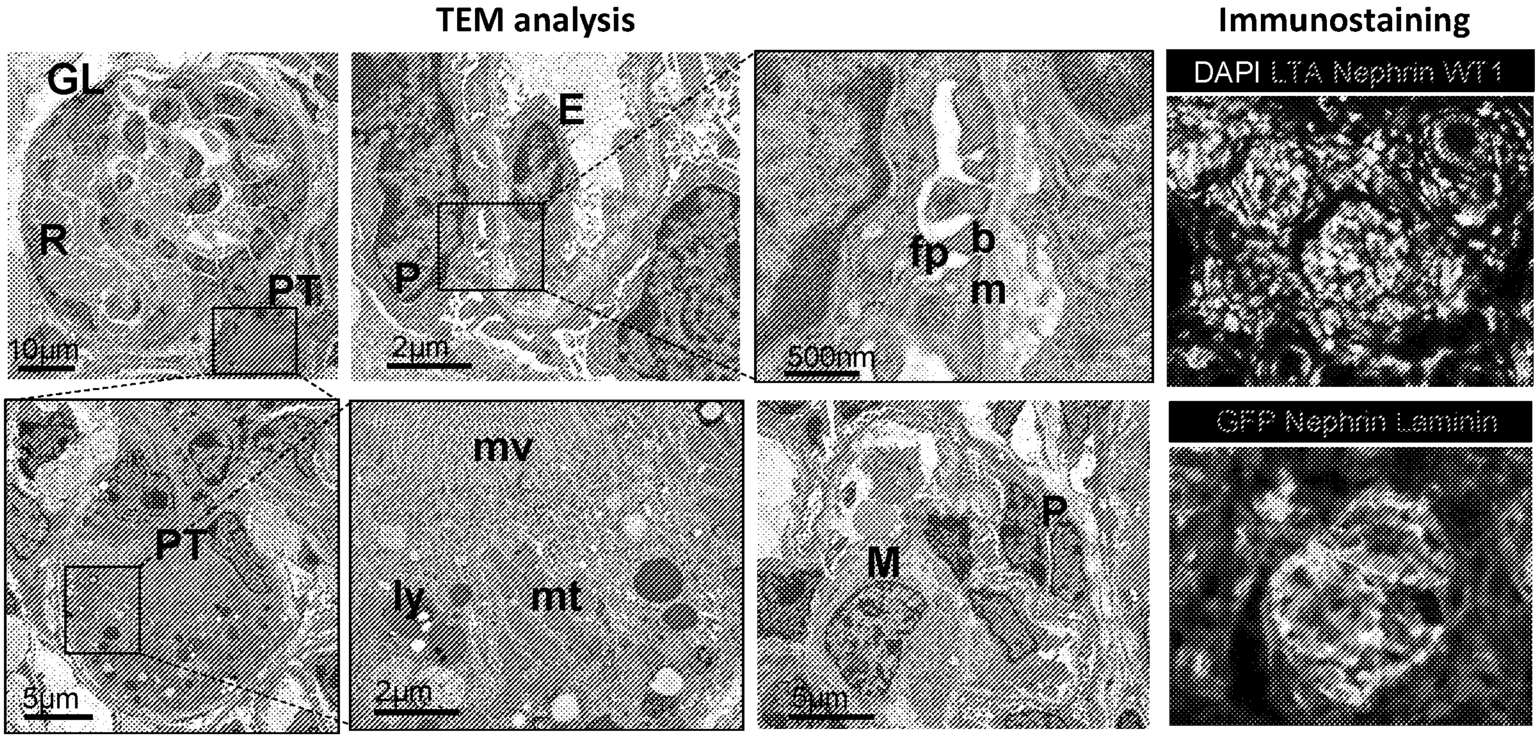

FIG. 17 Structural analysis of kidney primordium that matured after transplantation.

Figure 18:
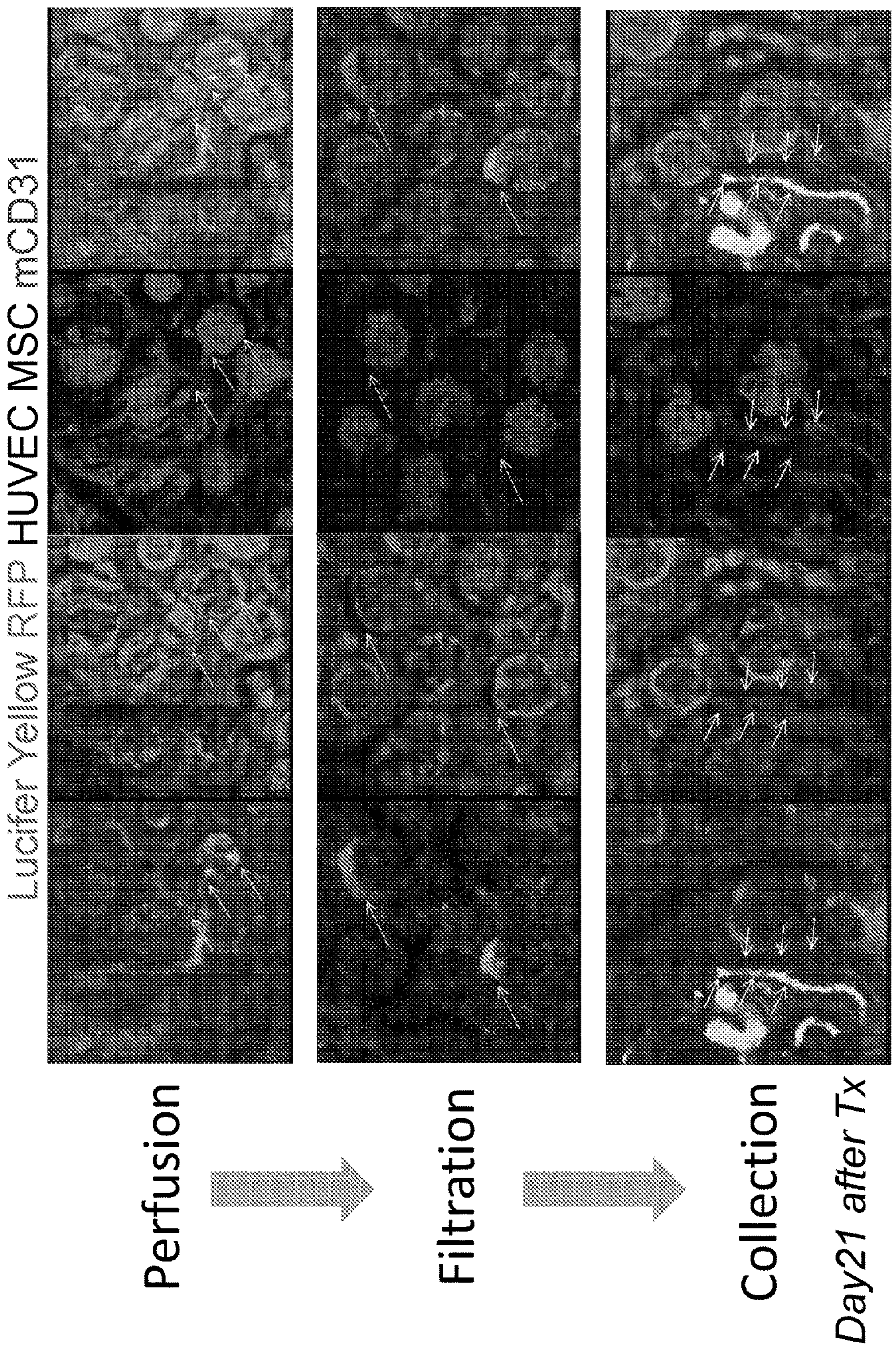

FIG. 18 Live imaging of the capacity of the transplanted kidney primordium to produce primitive urine.

Figure 19:
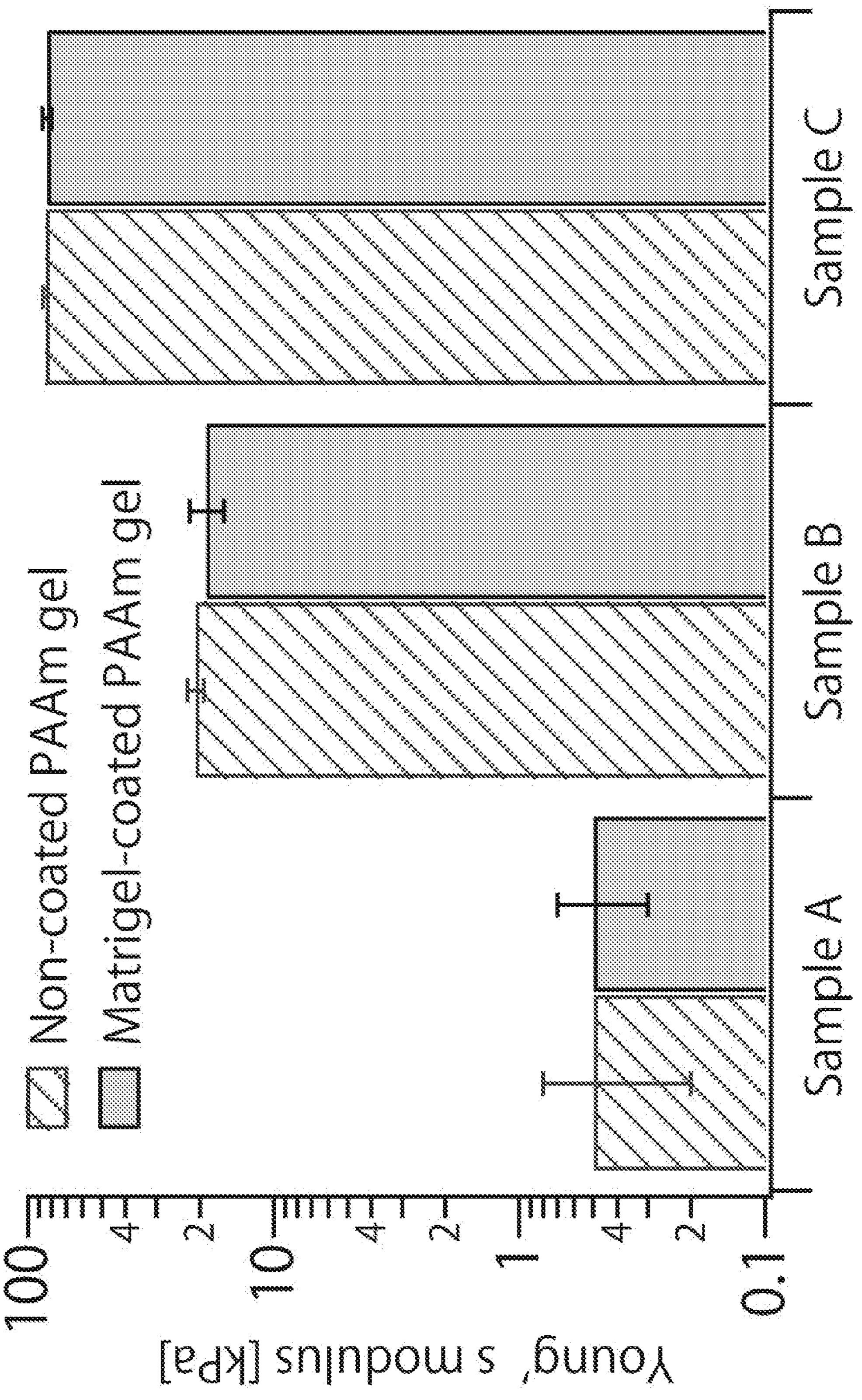

FIG. 19 Measurements of stiffness properties before and after coating with a biochemical substance.

Figure 20:
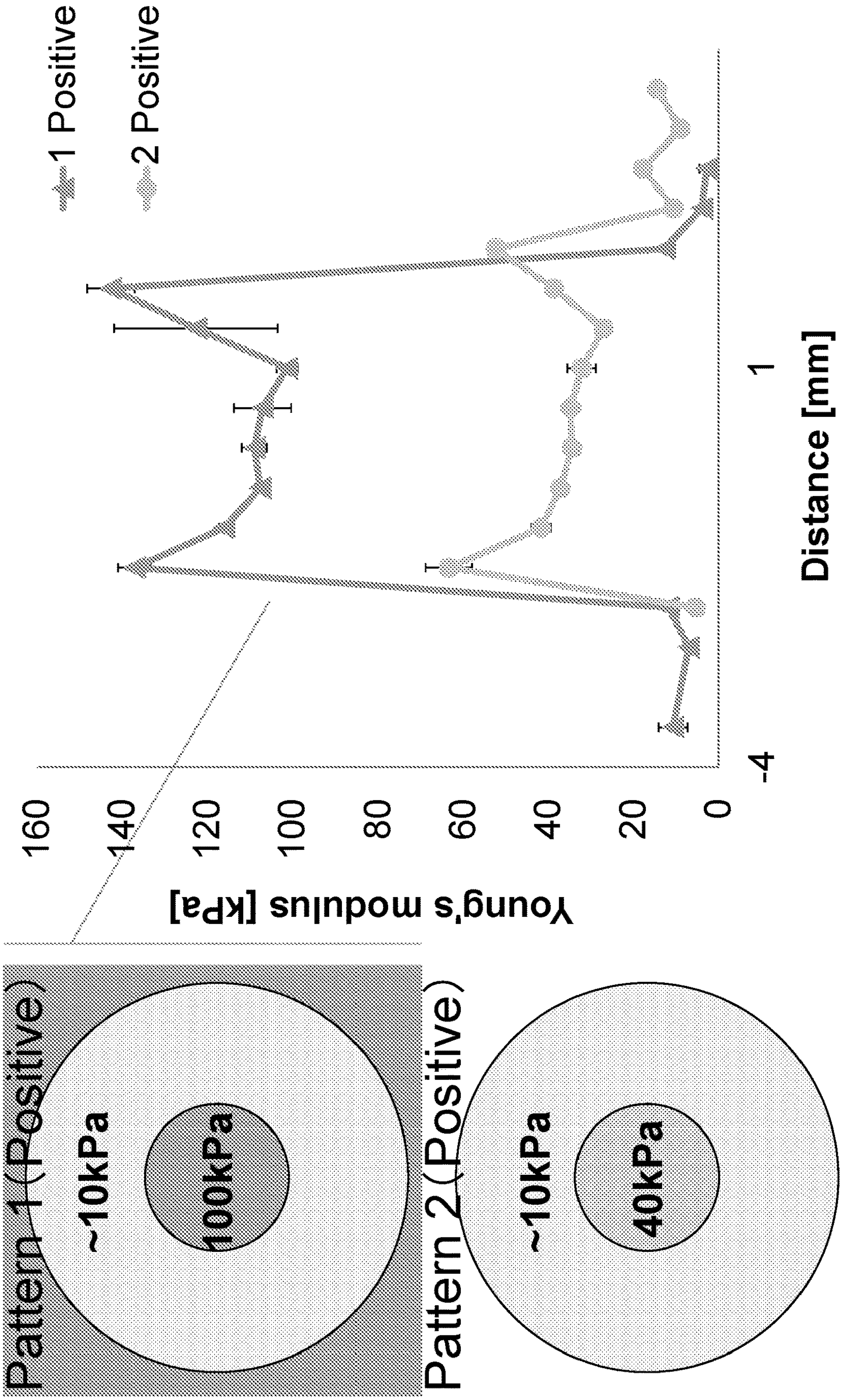

FIG. 20 Preparation of supports having multiple patterns of stiffness.

Figure 21:
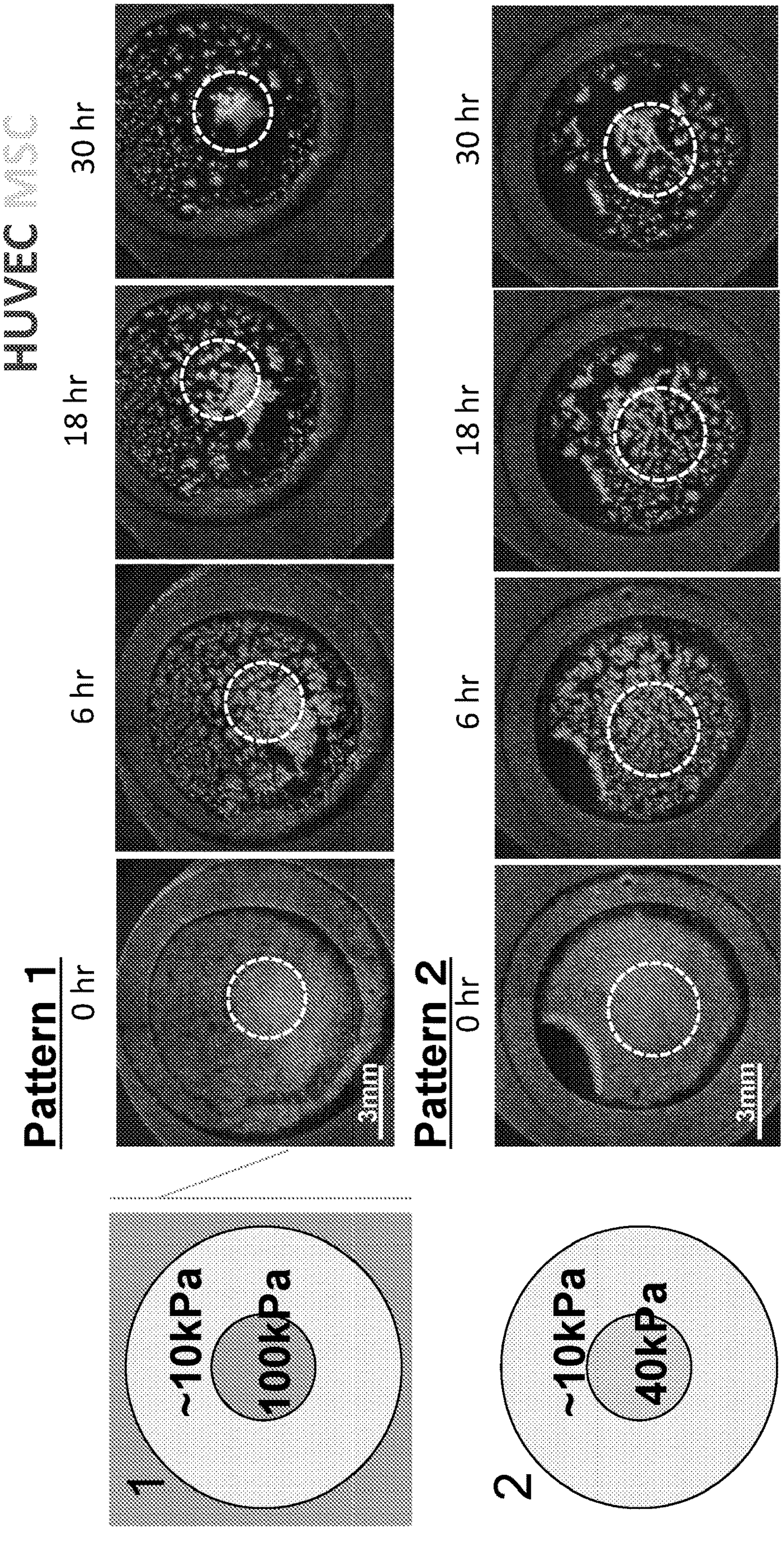

FIG. 21 Preparation of cell condensates on supports having multiple patterns of stiffness.

Figure 22:
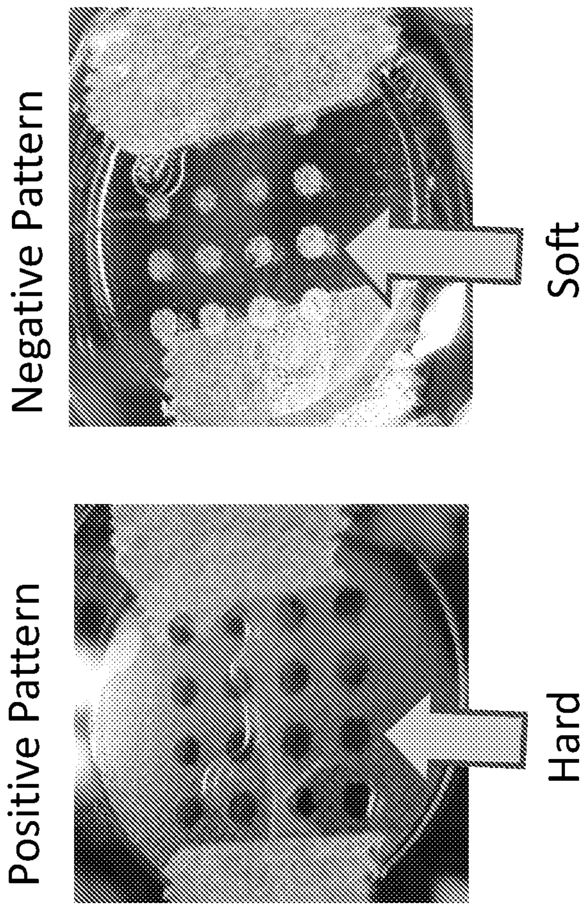

FIG. 22 Preparation of supports having complex multiple patterns.

BEST MODES

Hereinbelow, the present disclosure will be described in detail.

The present disclosure provides an organ bud prepared from vascular cells, mesenchymal cells and tissue or organ cells, wherein each of the vascular cell, the mesenchymal cell and the tissue or organ cell has been induced from pluripotent stem cells.

In the present disclosure, the term "organ bud" means a structure capable of differentiating into an organ through maturing, the structure comprising three types of cells which are vascular cells, mesenchymal cells and tissue or organ cells. Whether a structure is an organ bud or not can be judged, for example, by transplanting the structure into an organism and examining whether or not it is capable of differentiating into an organ of interest (the structure can be judged as organ bud if it has differentiated into the organ of interest); and/or by examining whether or not the structure comprises all of the above-described three types of cells (the structure can be judged as organ bud if it comprises all of the three types of cells). The organ bud may be one which differentiates into an ectodermal organ such as brain, spinal cord, adrenal medulla, epidermis, hair/nail/dermal gland, sensory organ, peripheral nerve or lens; a mesodermal organ such as spleen, kidney, urinary duct, heart, blood, gonad, adrenal cortex, muscle, skeleton, dermis, connective tissue or mesothelium; or an endodermal organ such as liver, pancreas, digestive tract (pharynx, esophagus, stomach, intestinal tract), lung, thyroid, parathyroid, urinary tract or thymus. Preferably, the organ bud is one which differentiates into an endodermal organ; e.g., one which differentiates into liver (liver bud), one which differentiates into pancreas (pancreas bud), or one which differentiates into intestinal tract. Whether an organ bud is one which differentiates into an endodermal organ or not can be judged by examining the expression of marker proteins (if any one or a plurality of the marker proteins described later are expressed, the organ bud can be judged as the organ bud of interest). For example, HHEX, SOX2, HNF4A, AFP, ALB and the like are markers for liver buds; PDX1, SOX17, SOX9 and the like are markers for pancreas bud; and CDX2, SOX9 and the like are markers for organ buds which differentiate into intestinal tract. Among the terms used by those skilled in the art, the following are included in the organ bud of the present disclosure: liver bud, liver diverticula, liver organoid, pancreatic (dorsal or ventral) buds, pancreatic diverticula, pancreatic organoid, intestinal bud, intestinal diverticula, intestinal organoid (K. Matsumoto, et al. Science. 19; 294 (5542): 559-63 (2001)) and so on.

The organ bud of the present disclosure is prepared from vascular cells, mesenchymal cells and tissue or organ cells, all of these three types of cells being entirely derived from pluripotent stem cells.

As pluripotent cells, the following may be enumerated, for example: pluripotent cells obtained from organisms [e.g., ES cells, pluripotent cells induced by reprogramming such as iPS cells, MUSE cells (Multilineage-differentiating stress-enduring (Muse) cells are a primary source of induced pluripotent stem cells in human fibroblasts. PNAS, 2011), iMPC cells (induced multipotent progenitor cell; Mouse liver repopulation with hepatocytes generated from human fibroblasts. Nature, 2014)] and a combination thereof.

Pluripotent stem cells may be human-derived. Alternatively, pluripotent cells may also be derived from non-human animals (e.g., animals used as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab and the like).

The organ bud of the present disclosure may be prepared by co-culturing in vitro three types of cells (vascular cells, mesenchymal cells and tissue or organ cells) induced from pluripotent stem cells. The present disclosure provides a method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

In the present disclosure, the term "tissue or organ cell" is a concept encompassing cells differentiated into functional cells constituting tissues or organs, or undifferentiated cells which are capable of differentiating into such functional cells. Undifferentiated cells include stem cells, progenitor cells, endoderm cells, organ bud cells, and so on. Preferably, undifferentiated cells are those cells which are destined to, but are yet to, differentiate into functional cells. Examples of "undifferentiated tissue or organ cell" include, but are not limited to, cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/dermal gland, sensory organ, peripheral nerve or lens; cells capable of differentiating into a mesodermal organ such as spleen, kidney, urinary duct, heart, blood, gonad, adrenal cortex, muscle, skeleton, dermis, connective tissue or mesothelium; and cells capable of differentiating into an endodermal organ such as liver, pancreas, digestive tract (pharynx, esophagus, stomach, intestinal tract), lung, thyroid, parathyroid, urinary tract or thymus. Whether or not a certain cell is capable of differentiating into an ectodermal organ, mesodermal organ or endodermal organ can be determined by checking for the expression of marker proteins (if any one or more of marker proteins are expressed, the cell can be judged as a cell capable of differentiating into an ectodermal organ, mesodermal organ or endodermal organ). For example, in cells capable of differentiating into liver, HHEX, SOX2, HNF4A, AFP, ALB and the like are markers; in cells capable of differentiating into pancreas, PDX1, SOX17, SOX9 and the like are markers; in cells capable of differentiating into intestinal tract, CDX2, SOX9 and the like are markers; in cells capable of differentiating into kidney, SIX2 and SALL1 are markers; in cells capable of differentiating into heart, NKX2-5, MYH6, ACTN2, MYL7 and HPPA are markers; in cells capable of differentiating into blood, C-KIT, SCA1, TER119 and HOXB4 are markers; and in cells capable of differentiating into brain or spinal cord, HNK1, AP2, NESTIN and the like are markers. Among the terms used by those skilled in the art, the following are included in the "undifferentiated tissue or organ cell" of the present disclosure: hepatoblast, hepatic progenitor cells, hepatic precursor cells, pancreatoblast, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cells, cardiac mesoderm, cardiovascular progenitor cells, cardiac progenitor cells (JR. Spence, et al. Nature; 470(7332):105-9. (2011); Self, et al. EMBO J.; 25(21): 5214-5228. (2006); J. Zhang, et al. Circulation Research.; 104: e30-e41(2009); G. Lee, et al. Nature Biotechnology 25, 1468-1475 (2007)) and so on. Undifferentiated cells may be prepared from pluripotent stem cells such as induced pluripotent stem cells (iPS cells) or embryonic stem cells (ES cells) by known methods. For example, cells capable of differentiating into liver may be prepared as previously described (K. Si-Taiyeb, et al. Hepatology, 51 (1): 297-305(2010); T. Touboul, et al. Hepatology. 51 (5):1754-65 (2010)); cells capable of differentiating into pancreas may be prepared as previously described (D. Zhang, et al. Cell Res.; 19(4):429-38 (2009)); cells capable of differentiating into intestinal tract may be prepared as previously described (J. Cai, et al. J Mol Cell Biol.; 2(1): 50-60 (2010); R. Spence, et al. Nature.; 470 (7332):105-9 (2011)); cells capable of differentiating into heart may be prepared as previously described (J. Zhang, et al. Circulation Research.; 104: e30-e41(2009); and cells capable of differentiating into brain or spinal cord may be prepared as previously described (G. Lee, et al. Nature Biotechnology 25, 1468-1475 (2007)). Examples of functional cells constituting organs or tissues include, but are not limited to, endocrine cells of pancreas, pancreatic duct epithelial cells of pancreas, hepatocytes of liver, epithelial cells of intestinal tract, tubular epithelial cells of kidney, podocytes of kidney, cardiomyocytes of heart, lymphocytes and granulocytes of blood, erythrocytes, neurons and glial cells of brain, and neurons and Schwann cells of spinal cord.

In the preparation of the organ bud of the present disclosure, tissue or organ cells prepared (induced by directed differentiation) from pluripotent stem cells are used.

With respect to directed differentiation from pluripotent stem cells (e.g., iPS cells) into hepatic endoderm cells (iPSC-HE), hepatic function has been greatly improved by using day 7 TBX3 and ADR1AB co-positive cells based on comparison of differentiation stages (see Example described later).

In the present specification, expressions such as "positive" or "+" used with respect to cell surface markers refer to a state in which expression of the relevant cell surface marker on the cell can be confirmed by immunostaining or the like. On the other hand, expressions such as "negative" or "−" refer to a state in which expression of the relevant marker cannot be confirmed by immunostaining or the like.

In another aspect, the present disclosure provides a method of preparing a cell condensate in vitro, comprising culturing a mixture of cells and/or tissues of a desired type and mesenchymal cells to form a cell condensate.

Mesenchymal cells are connective tissue cells that are mainly located in mesoderm-derived connective tissues and which form support structures for cells that function in tissues. In the present specification, the term "mesenchymal cell" is a concept that encompasses those cells which are destined to, but are yet to, differentiate into mesenchymal cells. Mesenchymal cells to be used in the present disclosure may be either differentiated or undifferentiated. Preferably, undifferentiated mesenchymal cells are used. Whether a cell is an undifferentiated mesenchymal cell or not can be determined by checking to see if the cell expresses marker proteins such as Stro-1, CD29, CD44, CD73, CD90, CD105, CD133, CD271 or Nestin (if any one or more of the above-listed marker proteins are expressed, the cell can safely be regarded as an undifferentiated mesenchymal cell). A mesenchymal cell in which none of the above-listed markers is expressed can be regarded as a differentiated mesenchymal cell. Among the terms used by those skilled in the art, the following are included in the "mesenchymal cell" of the present disclosure: mesenchymal stem cells, mesenchymal progenitor cells, mesenchymal cells (R. Peters et al. PLoS One. 30; 5(12):e15689 (2010)) and so on. As mesenchymal cells, human-derived ones are mainly used. However, mesenchymal cells derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used.

The cells and/or tissues of a desired type to be mixed with mesenchymal cells are independent of the types or numbers to be combined and may be any cells and/or tissues. Moreover, the origin of such cells and/or tissues also does not matter and they may be derived from any organ (e.g. liver, pancreas, intestine, lung, kidney, heart and brain) or any tissue; alternatively, they may be derived from cancer. Cells to be mixed with mesenchymal cells may be functional cells which constitute organs or tissues, or undifferentiated or pluripotent cells which will differentiate into functional cells. Further, tissues to be mixed with mesenchymal cells may be tissues isolated from individuals, or tissues induced from functional cells which constitute organs or tissues, or tissues induced from undifferentiated or pluripotent cells which will differentiate into functional cells.

Undifferentiated cells may be cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/dermal gland, sensory organ, peripheral nerve or lens; cells capable of differentiating into a mesodermal organ such as kidney, urinary duct, heart, blood, gonad, adrenal cortex, muscle, skeleton, dermis, connective tissue or mesothelium; and cells capable of differentiating into an endodermal organ such as liver, pancreas, intestine, lung, thyroid, parathyroid or urinary tract. Whether or not a cell is capable of differentiating into an ectodermal organ, mesodermal organ or endodermal organ can be determined by checking for the expression of marker proteins (if any one or a plurality of marker proteins are expressed, the cell can be regarded as a cell capable of differentiating into an endodermal organ). For example, cells capable of differentiating into liver have such markers as HHEX, SOX2, HNF4A, AFP and ALB; cells capable of differentiating into pancreas have such markers as PDX1, SOX17 and SOX9; cells capable of differentiating into intestine have such markers as CDX2 and SOX9; cells capable of differentiating into kidney have such markers as SIX2 and SALL1; cells capable of differentiating into heart have such markers as NKX2-5, MYH6, ACTN2, MYL7 and HPPA; cells capable of differentiating into blood have such markers as C-KIT, SCA1, TER119 and HOXB4; and cells capable of differentiating into brain or spinal cord have such markers as HNK1, AP2 and NESTIN. Among the terms used by those skilled in the art, the following are included in the "undifferentiated cell" of the present disclosure: hepatoblast, hepatic progenitor cells, pancreatoblast, hepatic precursor cells, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cells, cardiac mesoderm, cardiovascular progenitor cells, cardiac progenitor cells (J R. Spence et al. Nature.; 470(7332):105-9. (2011); Self et al. EMBO J.; 25(21): 5214-5228. (2006); J. Zhang et al. Circulation Research.; 104: e30-e41 (2009); G. Lee et al. Nature Biotechnology 25, 1468-1475 (2007)) and so on. Examples of pluripotent cells include pluripotent cells obtained from living bodies (e.g., ES cells), pluripotent cells obtained by induction from reprogramming [e.g., iPS cells, STAP cells (Stimulus-triggered fate conversion of somatic cells into pluripotency. Nature, 2014), MUSE cells (Multilineage-differentiating stress-enduring (Muse) cells are a primary source of induced pluripotent stem cells in human fibroblasts. PNAS, 2011), iMPC cells (induced multipotent progenitor cell; Mouse liver repopulation with hepatocytes generated from human fibroblasts. Nature, 2014)] and combinations thereof. Undifferentiated cells may be prepared from pluripotent stem cells such as induced pluripotent stem cells (iPS cells) or embryonic stem cells (ES cells) according to known methods. For example, cells capable of differentiating into liver may be prepared as previously described (K. Si-Taiyeb et al. Hepatology, 51 (1): 297-305 (2010); T. Touboul et al. Hepatology. 51 (5):1754-65 (2010)); cells capable of differentiating into pancreas may be prepared as previously described (D. Zhang et al. Cell Res.; 19(4):429-38 (2009)); cells capable of differentiating into intestine may be prepared as previously described (J. Cai et al. J Mol Cell Biol.; 2(1):50-60 (2010); R. Spence et al. Nature.; 470 (7332):105-9 (2011)); cells capable of differentiating into heart may be prepared as previously described (J. Zhang et al. Circulation Research.; 104: e30-e41 (2009); and cells capable of differentiating into brain or spinal cord may be prepared as previously described (G. Lee et al. Nature Biotechnology 25, 1468-1475 (2007)). Examples of functional cells that constitute organs or tissues include endocrine cells in pancreas, pancreatic duct epithelial cells in pancreas, hepatocytes in liver, epithelial cells in intestine, tubular epithelial cells in kidney, glomerular epithelial cells in kidney, cardiomyocytes in heart, lymphocytes, granulocytes and erythrocytes in blood, neurons and glial cells in brain, as well as neurons and Schwan cells in spiral cord. Human-derived cells are mainly used, but cells derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used.

When a cell condensate need be provided with a vascular system, vascular cells may be added to a mixture of cells and/or tissues of a desired type with mesenchymal cells. Vascular cells may be isolated from vascular tissues but they are in no way limited to those isolated from vascular tissues. Vascular cells may be derived from totipotent or pluripotent cells (such as iPS cells and ES cells) by directed differentiation. As vascular cells, vascular endothelial cells are preferable. In the present specification, the term "vascular endothelial cells" means cells that constitute vascular endothelium or cells that are capable of differentiating into such cells (for example, vascular endothelial progenitor cells and vascular endothelial stem cells). Whether a cell is a vascular endothelial cell or not can be determined by checking to see if it expresses marker proteins such as TIE2, VEGFR-1, VEGFR-2, VEGFR-3, VE-cadherin and CD31 (if any one or more of the above-listed marker proteins are expressed, the cell can safely be regarded as a vascular endothelial cell). Further, as markers for vascular endothelial progenitor cells, c-kit, Sca-1, etc. have been reported. If these markers are expressed, the cell of interest can be identified as a vascular endothelial progenitor cell (S. Fang et al., PLOS Biology, 2012; 10(10): e1001407). Among the terms used by those skilled in the art, the following are included in the "vascular endothelial cell" of the present disclosure: endothelial cells, umbilical vein endothelial cells, endothelial progenitor cells, endothelial precursor cells, vasculogenic progenitors, hemangioblast (H J. Joo et al. Blood. 25; 118(8): 2094-104 (2011)) and so on. As vascular cells, human-derived cells are mainly used. However, vascular cells derived from non-human animals (e.g., animals used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab or the like) may also be used. Vascular cells may be obtained from umbilical cord blood, umbilical cord vessels, neonatal tissues, liver, aorta, brain, bone marrow, adipose tissues, and so forth.

In the present specification, the term "vascular system" refers to a structure composed of vascular endothelial cells and their supporting cells. Vascular systems not only maintain tissues but also play an important role in the maturation process of tissues. Vascular structures have such a role that, once transplanted, they supply the interior of tissues with oxygen and nutrients that are necessary for their survival. What is more, it is believed that even before blood flows into the tissue, recapitulating three-dimensional tissue structures and cell polarities that are accompanied by blood vessels is important for the differentiation, proliferation and maintenance of cells. Therefore, avascular tissues not only fail to engraft upon transplantation, resulting in necrosis of their interior, but at the same time, tissue maturation associated with vascularization is not achieved. It has, therefore, been difficult for avascular tissues to exhibit adequate functions.

In the present specification, the terms "providing a vasculature system" and "vascularization" mean that a vascular system composed of vascular endothelial cells and their supporting cells is made directly integral with a target tissue. When a biological tissue that has been provided with a vascular system is transplanted into a living body, maturation of blood vessels is observed and upon connecting to the host blood vessels, blood perfusion starts, enabling the transplanted biological tissue to be directed to a functional tissue/organ having vascular networks.

In the present disclosure, a mixture of cells and/or tissues of a desired type (in a total cell count of 400,000 or more, preferably 400,000 to 4,400,000, and more preferably about 2,000,000) and mesenchymal cells (40,000 or more, preferably 50,000 to 1,000,000, and more preferably 100,000 to 400,000 cells) may be cultured. According to the method of the present disclosure, a cell condensate is formed autonomously and. Cell condensates of various sizes can be formed, e.g., in sizes of 1 mm or more (preferably 1-20 mm and more preferably 1-8 mm) The ratio between the cells and/or tissues of a desired type and the mesenchymal cells is not particularly limited as long as it falls within a range which permits formation of cell condensates of a desired size. An advantageous cell count ratio between the cells and/or tissues of a desired type and the mesenchymal cells is 10:0.5-3.

When vascular cells are added, 4,000 or more (preferably 20,000 to 400,000, more preferably about 40,000 to 280,000) vascular cells may be added to cells and/or tissues of a desired type (in a total cell count of 400,000 or more, preferably 400,000 to 4,400,000, and more preferably about 2,000,000) and mesenchymal cells (40,000 or more, preferably 50,000 to 1,000,000, and more preferably 100,000 to 400,000 cells). The ratio between the cells and/or tissues of a desired type, mesenchymal cells and vascular cells is not particularly limited as long as it falls within a range which permits formation of cell condensates of a desired size. An advantageous cell count ratio between the cells and/or tissues of a desired type, mesenchymal cells and vascular cells is 10:1-3:0.1-7.

The mixture of the cells and/or tissues of a desired type and the mesenchymal cells is capable of forming cell condensates in two-dimensional culture. The medium used for culture may be any medium that enables the formation of cell condensates. Preferably, the medium has a composition that promotes induction of self-organization into a tissue of interest. For example, when self-organization is to be induced by transplantation into a living body, a medium prepared by mixing a vascular endothelial cell culture medium and a medium for culturing the organ of interest at 1:1 may be used. Preferable examples of vascular endothelial cell culture media include, but are not limited to, EGM™ BulletKit™ (Lonza CC-4133) and EGM-2™, BulletKit (Lonza CC-3162), EGM-2™ and MV (Lonza CC-3156). Examples of media for culturing organs include, but are not limited to, RPMI1640 (Wako) supplemented with 20% fetal bovine serum (BWT Lot.S-1560), 100 μg/ml penicillin/streptomycin (Gibco) and Insulin-Transferrin-Selenium X (GIBCO), which may be used for adult renal cells. For culturing embryonic renal cells, D-MEM High-Glucose (Wako 043-30085), 10% fetal bovine serum (BWT Lot.S-1560), 100 μg/ml penicillin/streptomycin (Gibco), and the like may be preferably used.

The mixture of the cells and/or tissues of a desired type and the mesenchymal cells may be cultured on a gel-like support on which the mesenchymal cells are capable of contraction.

Contraction of mesenchymal cells may be confirmed, for example, by microscopically or macroscopically noting the formation of a 3D tissue morphologically or by showing that the tissue has such a strength that it retain its shape as it is collected as with a spatula (Takebe et al. Nature 499 (7459), 481-484, 2013).

The support may be a gel-like substrate having an appropriate stiffness [e.g., a Young's modulus of 200 kPa of less (in the case of a Matrigel-coated gel of a flat shape); however, the appropriate stiffness of the support may vary depending on the coating and shape]. Examples of such substrates include, but are not limited to, hydrogels (such as acrylamide gel, gelatin and Matrigel). The stiffness of the support need not be uniform and may vary depending on the shape, size and quantity of an condensate of interest. It is possible to provide the stiffness with a spatial/temporal gradient (as in Example 6 to be described later) or a pattern (as in Example 7 to be described later). When the stiffness of the support is uniform, it is preferably 100 kPa or less, more preferably 1-50 kPa. The gel-like support may be planar, or the side on which culture is to be performed may have a U- or V-shaped cross section. If the side of the gel-like support on which culture is to be performed has a U- or V-shaped cross section, cells tend to gather on the culture surface and a cell condensate can advantageously be formed from a smaller number of cells and/or tissues. Further, the support may be modified chemically or physically. Examples of modifying substances include, but are not limited to, Matrigel, laminin, entactin, collagen, fibronectin and vitronectin.

One example of the gel-like culture support that is provided with a spatial gradient of stiffness is a gel-like culture support whose stiffness in the central part is greater than the stiffness in the peripheral part (see Example 6 to be described later and FIGS. 20 and 21). Appropriately, the stiffness of the central part is 200 kPa or less and it suffices that the peripheral part is softer than the central part. Appropriate values for the stiffness of the central and peripheral parts of the substrate are variable depending on the coating and the shape. Another example of the gel-like culture support that is provided with a spatial gradient of stiffness is a gel-like culture support whose stiffness in the peripheral part is greater than the stiffness in the central part.

One example of the patterned, gel-like culture support is a gel-like culture support having one or more patterns in which the stiffness of the central part is greater than the stiffness of the peripheral part (see Example 7 to be described later; FIG. 22, left panel: positive pattern). Appropriately, the stiffness of the central part is 200 kPa or less; it suffices that the peripheral part is softer than the central part. Appropriate values for the stiffness of the central and peripheral parts of the substrate are variable depending on the coating and the shape. Another example of the patterned, gel-like culture support is a gel-like culture support having one or more patterns in which the stiffness of the peripheral part is greater than the stiffness of the central part (see Example 7 to be described later; FIG. 22, right panel: negative pattern). Appropriately, the stiffness of the peripheral part is 200 kPa or less; it suffices that the central part is softer than the peripheral part. Appropriate values for the stiffness of the central and peripheral parts of the substrate are variable depending on the coating and the shape.

The temperature at the time of culture is not particularly limited but it is preferably 30-40° C. and more preferably 37° C. When a larger tissue is to be cultured, an increased amount of oxygen is preferably supplied into the incubator. The amount of oxygen supply is appropriately 4-50%, preferably 10-30%, and more preferably 18-25%.

The culture period is not particularly limited but it is preferably 12-144 hr. For example, when formation of cell condensates 0.4-10 mm in size from cells and/or tissues isolated from liver is intended, the culture period is preferably 12-48 hr. When formation of cell condensates 0.4-10 mm in size from cells and/or tissues isolated from pancreas is intended, the culture period is preferably 12-144 hr. When formation of cell condensates 0.4-3 mm in size from cells and/or tissues isolated from intestine is intended, the culture period is preferably 12-96 hr. When formation of cell condensates 0.4-1 mm in size from cells and/or tissues isolated from lung is intended, the culture period is preferably 12-96 hr. When formation of cell condensates 0.4-10 mm in size from cells and/or tissues isolated from heart is intended, the culture period is preferably 12-96 hr. When formation of cell condensates 0.4-5 mm in size from cells and/or tissues isolated from kidney is intended, the culture period is preferably 12-144 hr. When formation of cell condensates 0.4-10 mm in size from cells and/or tissues isolated from brain is intended, the culture period is preferably 12-144 hr. When formation of cell condensates 0.4-10 mm in size from cells and/or tissues isolated from cancer is intended, the culture period is preferably 12-144 hr. Further, when formation of cell condensates 0.4-10 mm in size from pluripotent cells such as iPS cells is intended, the culture period is preferably 48-144 hr.

In the cell condensates prepared by the method of the present disclosure, cell-cell interactions have taken place in such a close manner that a biological environment as occurs in the womb is recapitulated. As a consequence, induction of early differentiation into organ progenitor cells occurs efficiently and this would improve the frequency and number of such cells. Further, in the cell condensates prepared by the method of the present disclosure, cells adhere to each other so strongly that they can be collected in a non-destructive manner.

The cell condensate described in the present application is a concept typically encompassing organ buds and organoids [organ bud (WO2013/047639), liver bud, liver diverticula, liver organoid, pancreatic (dorsal or ventral) buds, pancreatic diverticula, pancreatic organoid, intestinal bud, intestinal diverticula, intestinal organoid (K. Matsumoto et al. Science. 19; 294 (5542): 559-63 (2001)]. The cell condensates are independent of the types of constituent cells and the number of such types. However, organ buds correspond to cell condensates that are formed at an early stage of organogenesis and are in principle composed of the following three types of cells: functional cells that constitute organs or tissues (or undifferentiated cells which will differentiate into functional cells); vascular cells; and mesenchymal cells. Organoids are solely composed of cells that constitute epithelial tissues and they are basically of a small size (1 mm or less).

Cell condensates undergo self-organization to form three-dimensional tissue structures provided with higher structures, whereby progenitor cells can be directed to terminal differentiation. Self-organization may be performed either in vivo or in vitro. For example, when a cell condensate prepared by the method of the present disclosure is transplanted into a living body, vascular networks are formed, blood perfusion is induced, and self-organization into a higher tissue with a complex structure occurs, enabling the preparation of tissues/organs that have a highly ordered tissue structure comparable to that of adult tissues. With the cell condensate of the present disclosure, it may be possible to prepare a higher tissue that is provided with not only a vascular network but also higher structures such as ureteral structure, biliary structure, tracheal structure, etc. Further, a great number of organs essentially require that reconstitution associated with other organs be realized in order to exhibit their functions; e.g., in liver, reconstitution of junctions with bile duct and pancreatic duct and connection to duodenum is essential for exhibiting its function. According to the present disclosure, a cell condensate which recapitulates interactions with other organs is prepared. This cell condensate is expected to find use as a system for inducing self-organization into complex organs existing in the body.

The present disclosure also provides a cell condensate prepared by the above-described method.

Further, the present disclosure also provides a method of three-dimensional tissue structure, comprising allowing self-organization of a cell condensate prepared by the above-described method to form a three-dimensional tissue structure that has been provided with higher structures.

Further, the present disclosure also provides a gel-like culture support wherein the side on which culture is performed has a U- or V-shaped cross-section. The gel-like culture support of the present disclosure, having a U- or V-shaped cross-section on the side where culture is performed, allows cells to gather on the culture surface to ensure that a cell condensate is advantageously formed from a smaller number of cells and/or tissues. The gel-like culture support wherein the side on which culture is performed has a U- or V-shaped cross-section is as defined above.

The present disclosure also provides a gel-like culture support wherein the stiffness of the central part thereof is greater than the stiffness of the peripheral part thereof. One embodiment of such culture support is shown in Example 6 to be described later (FIGS. 20 and 21). Appropriately, the stiffness of the central part is 200 kPa or less; it suffices that the peripheral part is softer than the central part. Appropriate values for the stiffness of the central and peripheral parts of the support are variable depending on the coating and the shape.

The present disclosure also provides a gel-like culture support in which the stiffness of the peripheral part thereof is greater than the stiffness of the central part thereof.

The present disclosure also provides a gel-like culture support having one or more patterns in which the stiffness of the central part is greater than the stiffness of the peripheral part. One embodiment of such culture support is given in Example 7 to be described later (FIG. 22, left panel: positive pattern). Appropriately, the stiffness of the central part is 200 kPa or less; it suffices that the peripheral part is softer than the central part. Appropriate values for the stiffness of the central and peripheral parts of the support are variable depending on the coating and the shape.

The present disclosure also provides a gel-like culture support having one or more patterns in which the stiffness of the peripheral part is greater than the stiffness of the central part. One embodiment of such culture support is given in Example 7 described later (FIG. 22, right panel: negative pattern). Appropriately, the stiffness of the peripheral part is 200 kPa or less; it suffices that the central part is softer than the central part. Appropriate values for the stiffness of the central and peripheral parts of the support are variable depending on the coating and the shape.

Further, the present disclosure also provides a method of preparing a cell condensate in vitro, comprising culturing a mixture of cells and/or tissues of a desired type and mesenchymal cells on the above-described gel-like culture support to thereby form a cell condensate. Culturing of the mixture of the cells and/or tissues of a desired type and the mesenchymal cells is as defined above.

EXAMPLES

Hereinbelow, the present invention will be described in more detail with reference to the following Examples.

Example 1

It has been long held that formation of cell aggregation is an important principle for isolated immature cells to form a three-dimensional, complex organ via self-organization. The present inventors had found that liver primordia (of millimeter scale) were autonomously formed from isolated human liver progenitor cells in vitro by recapitulating the cell-cell interactions which would occur at organogenesis stages. However, the mechanism underlying such dynamic three-dimensional organization were totally unknown. The present inventors revealed that this 3D tissue formation started from self-assembly behavior of multiple cell units and that the presence of the cytoskeletal contractile force of myosin II occurring in mesenchymal stem cells was crucial for the progress of such behavior. *Ibis* dynamic cell collective behavior is regulated by the stiffness conditions of substrate matrix. Further, the present inventors succeeded under optimized substrate conditions in preparing three-dimensional organ primordia from cells/tissues isolated from diverse organs including liver, pancreas, intestine, lung, heart, kidney, brain and even cancer. The thus prepared three-dimensional primordia were immediately vascularized upon transplantation (since vascular endothelial cells had been incorporated therein), followed by autonomous formation of self-organized three-dimensional tissue structures having therapeutic effects. Toward the goal of regenerative medicine in future, this principle will serve to establish a highly versatile platform for reconstituting a plurality of vascularized, complex organ systems from stem cells via dynamic cell condensation and the subsequent self-organization.

It is known that liver is formed from a condensed tissue mass termed "liver bud" at week 5-8 of gestation in human during physiological organogenesis. Cell-cell interactions between mesenchymal stem cells, undifferentiated vascular endothelial cells and anterior visceral endoderm cells are required for the initiation of liver regeneration termed "liver budding" (also called "liver bud") in the foregut (1). In parallel with these basic understandings in organogenesis, recent advances in regenerative medicine have also demonstrated that this dynamic three-dimensional (3-D) rearrangement can be mimicked by recapitulating cellular interactions at organogenesis stages in culture using pluripotent stem cells (PSCs). When plated on a solidified soft matrix gel, single PSC-derived hepatocytes autonomously form 3-D condensates by co-culture with endothelial cells and mesenchymal cells (2). Once condensates are established, they continue to self-organize after several days under complete in vitro conditions into liver bud tissues having a structure resembling the organs that exist in the womb (3). The in vitro grown organ bud is transplanted into a living body, where it undergoes further self-organization (is matured) to eventually become a vascularized and functional liver. This method opens a new road for artificial reconstitution of vascularized organ systems (4). The most attractive aspect of these previous observations was that, in spite of the culture on a flat two-dimensional culture plate, considerably great morphogenetic changes were found in the cocultured cells. In the preceding studies of self-organization, condensates of micron scale were generally produced in 96-well plates with steep bottoms. In the system under consideration, however, condensates are capable of growing up to millimeter or even centimeter scale (5, 6). It was therefore the principal object of the present study to analyze the mechanism working at the center of this surprisingly dynamic assembling behavior and to elucidate crucial factors for recapitulating the phenomenon of interest. And under optimized conditions, the present inventors assessed the expandability of this approach ultimately aiming to reconstitute other organ systems.

Figure 1:
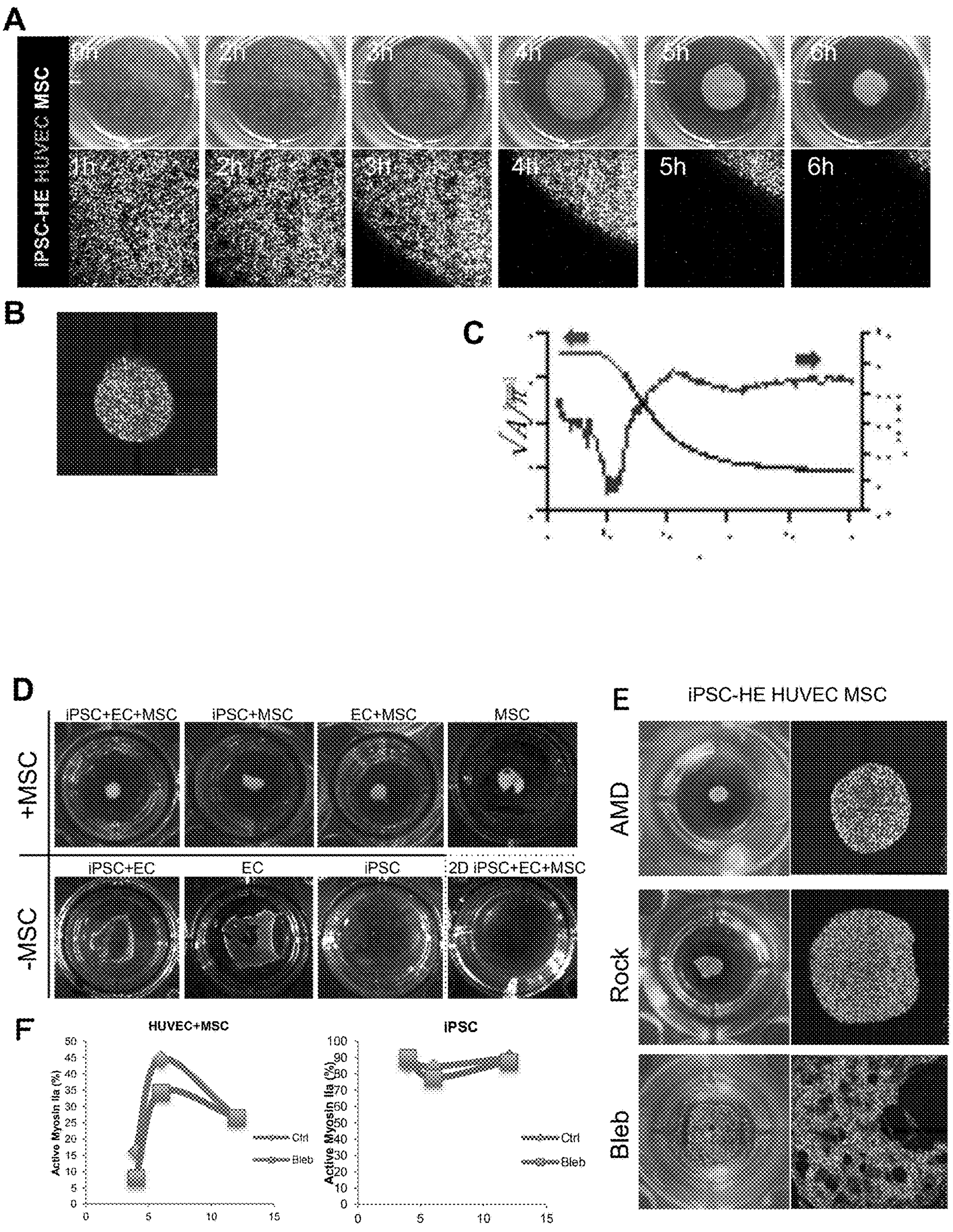
FIG. 1 Preparation of cell condensates via contraction of mesenchymal cells (A) Time-dependent changes in the process of formation of cell condensates. (Green) iPSC-hepatic endoderm cells; (Light red) human vascular endothelial cells; (Colorless) mesenchymal cells.

First, the present inventors performed a time-lapse imaging analysis to track cellular movements during organoid formation. Hepatic endoderm cells derived from human induced pluripotent stem cells (iPSCs), umbilical cord-derived endothelial cells (HUVECs), and mesenchymal stem cells (MSCs) were labeled with distinctive fluorescent markers and cocultured on a solidified matrix gel which was already described. Live cell tracking revealed that after rapid cell convergence, the assembly of vascularized organoids was initiated; this was followed by spatial rearrangements via self-organization as demonstrated by the formation of an endothelial-like network (FIG. 1). Briefly, during the initial self-convergent phase, it was discovered that cells behave as a cohesive multicellular unit and quickly travel to a single center (FIG. 1). To elucidate dynamics of such condensate formation in more detail, the present inventors examined the temporal development of the position of the edge of the cell condensate (square root of cell area) and circularity by image analysis (FIG. 1*b*). The results showed that cell condensates contracted gently at 10 μm/h or less up to about 7 hr after seeding, and then the contraction accelerated to about 500 μm/h at naxunyn over the next several hours and finally decreased exponentially to converge. On the other hand, its circularity decreased almost monotonically right after cell seeding and reached a minimal value of about 0.5 in 10-13 hr. The circularity then increased and finally achieved an almost constant value (0.85) at 20 hr after seeding.

The results described so far suggest that the formation of the condensate in the present study is based not on cell migration but on cell tissue contraction. First, the maximum velocity of the condensate edge reached as high as about 500 μm/h at 10-15 hr after cell seeding which is much higher than general cell migration velocity. Finally, the velocity decreased exponentially, but this suggests that the condensate is contracting in line with Kelvin-Voigt model, a dynamic model shown by an exponential function. Indeed, it has been shown that contraction of diverse cell tissues and stress fibers can be approximated with Kelvin-Voigt model. About 10 hr was required for the initiation of large-scale contraction of the condensate, which is assumed to be reasonable as a time for the progress of cell-cell adhesion and formation of stress fiber necessary for contraction. Indeed, the circularity results indicated that the shape of the condensates deviated from an exact circle during the early 10 hr, causing them to contract in distorted forms. This is believed to suggest that the contraction force at early stages of condensate formation is equal to or below the adhesion strength of cell-extracellular environment (cell-substrate and cell-container wall).

To identify the cell types which are critical for initiating this dynamic and directed cell condensation phenomenon, the present inventors examined all the possible combinations of the three cell lineages in coculture. As a result, it was found that lack of mesenchymal stem cells (MSCs) leads to a failure in condensate formation (iPSC+EC, EC, iPSC in FIG. 1). On the other hand, combination with MSCs is a sufficient condition for cell condensate formation, but the presence of vascular endothelial cells is not essential. For example, cell condensate formation was possible in coculture of iPSC-derived hepatic endoderm cells and MSC (iPSC+MSC) or coculture of vascular endothelial cells and MSC (EC+MSC) (FIG. 1). Although condensates were formed even in single MSC culture, culture groups without MSC simply produced sheet-like fragile tissues in any of the following groups: EC alone, iPSC alone, and iPSC+EC. Since it was impossible to collect such fragile tissues in a non-destructive manner, no condensates were formed. Condensate formation was not recognized also when cells were not cultured on a support (2-D, iPSC+EC+MSC). To elucidate the "contraction mechanisms" implied by the above-described observation, the present inventors subsequently assessed the contributions of the contraction force of MSCs at the molecular level against their substratum and the surrounding cells. During embryonic invagination in early developmental process, a group of cells undergoes contraction and it is known that the drastic inward displacement of cell-cell junctions is driven by myosin II (MID activity, allowing cells to invaginate during embryonic gastrulation. The present inventors therefore assessed MII activity by measuring time-course-dependent changes in MIIA phosphorylation with MIIA inactivating S1943 (pS1943) through decomposition of myofilament by phosphate-specific antibodies (7) and intracellular flow cytometry. Based on the formula reported to estimate MIIA activity (8), the present inventors showed that active MIIA was remarkably up-regulated in stromal cells during condensate formation and reached its peak at 6 hr, which corresponds to the time at which cells moved at maximum velocity (1). On the other hand, it is seen that activated MIIA is almost constant throughout condensate formation in iPSC-derived hepatocytes. This suggests that the MSC-driven activation of MIIA is responsible for this strong three-dimensional rearrangement. As data indicating direct evidence for the decrease of this activated MIIA, the present inventors showed that this condensate formation could be completely antagonized by treatment with blebbistatin (an MII ATPase inhibitor) (9). Similarly, it was found that addition of Rho kinase inhibitor Y-27632 to the cocultures partially delayed condensate formation (FIG. 1). On the other hand, with respect to the recently reported collective cell migration mechanism by an autonomously generated chemokine gradient during organogenesis (1), it was assumed that such mechanism is hard to apply because pharmacological inhibition of chemokine receptor pathways by addition of AMD3100 could not hinder condensate formation (10). These results revealed that the contraction force produced by actomyosin cytoskeleton plays an important role in the directed and drastic movements of cell condensates.

It is suggested at the single cell level that such cellular cytoskeletal contraction in culture is balanced by the degree of attachment to the anchoring matrix (11). Briefly, recent studies measuring the traction force of single cells have shown that cytoskeletal tension can be modulated by the biochemical and biophysical parameters of the substratum (12). Therefore, the present inventors assumed that the modulation of substratum hardness conditions could alter the collective behavior of the cultured cells if this process is also applicable to the contraction mechanism in cell condensation. In their preceding studies, the inventors tested various biochemical conditions using hydrogels, collagens, laminin, entactin, and combinations thereof and showed that a basement membrane composite, such as Matrigel, is the most efficient matrix. To further clarify the essential parameters, the present inventors assessed the effect of the biophysical stiffness of substrate. Specifically, to assess the effect of the outer environment on cell response, hydrogels were prepared whose biochemical/dynamic conditions were freely tunable (FIG. 2)(13). Cells were plated on the above-prepared substrates with diverse stiffness conditions. After incubation for about 24 hr, significant differences in collective behavior were already discernible. Briefly, when the movement of MSCs during condensate formation were traced to analyze velocity and order parameter, it became clear that both the velocity and order parameters exhibited maxima at E=17 kPa. These results clearly show that the stiffness of the extracellular environment is one of the critical parameters in condensate formation. Indeed, MSCs that are the key cell in condensate formation in the system of the present disclosure are known to exhibit mechano-response in diverse processes including differentiation and attachment. Generally, for the formation of condensates such as spheroids, cell-cell interactions must exceed cell-extracellular interactions and this condition may have been realized in the present system by the extracellular stiffness environment of E=17 kPa. Considering the necessity of MSC (FIG. 1), the present inventors have concluded that contraction of mesenchymal cells against softer substrate might have caused these collective behaviors in coculture systems.

Considering that the MSC-derived contraction force plays a central role in the above-described self-assembly behavior, it may be assumed that the proposed principle can be expanded to self-organization systems for other organs irrespective of the origin of germ layers that are to be used in the future for the purpose of regenerative medicine. To validate this hypothesis, the present inventors first selected pancreatic cells and subjected them to coculture, since there is increasing evidence that pancreas follows a developmental program relatively close to that of liver. When isolated mouse pancreas β cells (MIN6) were cocultured with HUVEC and MSC, a similar formation of cell condensate was observed (FIG. 3). To visualize the internal structure of the generated organoids, confocal microscopic analyses were performed with fluorescence-labeled cells. 3-D Z-stack images revealed that kusabira Orange (KO)-labeled MIN6 self-organized in 72 hr after transplantation to form islet-like tissues, whereas green fluorescence protein (EGFP)-labeled HUVEC formed a network structure covering the MIN6-derived islets inside the organoids. These results indicated a possibility that the operating principle found in liver might be extended to pancreas.

Next, to assess further versatility of this approach, the present inventors isolated multiple cells or tissue fragments (up to 200 μm) from embryonic or adult mice. Surprisingly, the directed and autonomic assembling phenomenon was retained in all the cell/tissue types tested, including pancreas, liver, intestine, lung, heart, kidney, brain, and even cancer (FIG. 3). Time-lapse imaging analyses revealed that both the embryonic and adult cells/tissues successfully resisted additional manipulations (including surgical transplantation) to form single 3D organoids autonomously (FIG. 3). Condensates as designed to contain cultured endothelial cells (HUVECs) turned out to permit a much more rapid perfusion with recipient circulation after transplantation (average perfusion time: ~72 hr) compared with reliable conventional tissue engineering approaches (average perfusion time: ~192 hr). These results suggest that scaffold-free and self-assembly approaches are superior in terms of vasculogenesis (FIG. 4). Although the presence of endothelial cells is dispensable for the generation of condensates, the post-transplant outcomes are clearly disappointing in the absence of HUVECs because no signs of functional vascularization are observed in vivo (FIG. 4).

Interestingly, most of adult organ cell-derived condensates, although retaining functional vascularization, failed to reconstitute tissues resembling the original tissues after transplantation (FIG. 7). However, embryonic cell-derived condensates efficiently reconstituted functional tissue units through self-organization. For example, transplantation of embryonic kidney-derived organoids reconstituted glomerular-like microtissues with signs of blood filtration (FIG. 4D), whereas adult kidney- or lung-derived condensates failed to produce such tissues (FIGS. 7 and 8). These results raise a question to the dominant paradigm in regenerative medicine that mature cell transplantation using cells directly differentiated from PSC might be effective for treating organ failures, because terminally differentiated cells have only poor ability to reconstitute functional tissues upon transplantation, even under well vascularized conditions.

Subsequently, the present inventors selected pancreatic cells for in-depth characterization. The transplantation of 3-D pancreatic organoids resulted in rapid (~48 hr) reperfusion and successful β cell engraftment. These were confirmed by live imaging analysis. After 14 days, the transplants developed islet-like structures (FIG. 4, E) with functional microvascular networks that connected to the recipient circulatory system (FIG. 4 C). Such blood perfusion was not recognized when condensates not containing vascular endothelial cells were transplanted (FIG. 9). The reconstituted islets directly connected to peripheral mouse blood vessels to be highly vascularized with a tight network of microvessels (FIG. 10). The capillary network in the islet in a living body is known to be approximately 5 times as dense as the capillary network surrounding exocrine secretion tissues. Consistent with this, intravital quantification of the functional vascular density showed that the capillary network was much denser (by 4.2 times) in the reconstituted islet-like tissues than in the areas surrounding the normal tissues (FIG. 4, FIG. 9). Histological analysis also showed that the islet-like tissues had a structure resembling the adult islet, suggesting the reconstitution of a mature tissue via self-organization (FIG. 11). Further, to evaluate their therapeutic efficiency, in vitro-derived β cell organoids were transplanted into kidney subcapsule of type 1 fulminant diabetic model mouse. As the diabetic model, the present inventors used a toxin receptor-mediated cell knockout (TREK) Tg mouse having a diphtheria toxin (DT) receptor cDNA transgene in insulin promoter. While mice in non-transplantation group died at day 6 of DT administration-mediated induction of diabetes, those mice which received transplantation of β cell organoids maintained normal blood glucose levels and survived (FIG. 4, G). Thus, the present inventors have demonstrated the applicability of the foregoing principle to other organ systems by experimentally recapitulating vascularization and reconstituting a functional three-dimensional tissue in vivo.

In the 1960s, aggregates of dissociated embryonic cells were shown to reconstitute tissues with a structure resembling that of the original tissue via self-organization. Once the required small numbers of various cells have aggregated to become capable of close interactions, individual cells are able to self-organize to form functional tissues in vitro (14). This classic knowledge about self-organization is capable of bringing about a technical revolution in the field of regenerative medicine which designs a principle for growing organs from PSC, one substantial challenge in this field. Now, this principle has been reinforced with observations of brain, optic cup, kidney and liver from PSC-derived cell aggregates by the present inventors and other researchers (15). In this context, the present inventors demonstrate one promising principle. Briefly, in contrast with conventional methods each enabling the formation of only small-size condensates (aggregates), the principle under consideration ensures that starting with larger numbers of the desired cells/tissues, self-organized organoids can be designed via condensation. The condensates may be used for examining the subsequent self-organization capacity both in vitro and in vivo. In the foregoing study, rapid vasculogenesis and subsequent functionalization were evaluated by incorporating endothelial cells experimentally. For more precise reconstruction of tissues, evaluating the contribution of undeveloped supporting cells such as neurons is also an interesting topic for the present inventors and other research groups. Although further improvement is necessary for determining optimal conditions for self-organization of tissues of interest, the present inventors believe that the culture principle described above not only provides a powerful tool for studying human biology and pathology using pluripotent stem cells but also enables realization of regenerative medicine of the next generation for currently untreatable patients by using in vitro grown, complex tissue structures.

References

1. K. Matsumoto, H. Yoshitomi, J. Rossant, K. S. Zaret, Liver organogenesis promoted by endothelial cells prior to vascular function. Science 294, 559 (Oct. 19, 2001).
2. T. Takebe et al., Self-organization of human hepatic organoid by recapitulating organogenesis in vitro. Transplant Proc 44, 1018 (May, 2012).
3. T. Takebe et al., Generation of a vascularized and functional human liver from an iPSC-derived organ bud transplant. Nature protocols 9, 396 (February, 2014).
4. T. Takebe et al., Vascularized and functional human liver from an iPSC-derived organ bud transplant. Nature 499, 481 (Jul. 25, 2013).
5. M. Eiraku et al., Self-organizing optic-cup morphogenesis in three-dimensional culture. Nature 472, 51 (Apr. 7, 2011).
6. T. Nakano et al., Self-formation of optic cups and storable stratified neural retina from human ESCs. Cell stem cell 10, 771 (Jun. 14, 2012).
7. N. G. Dulyaninova, R. P. House, V. Betapudi, A. R Bresnick, Myosin-IIA heavy-chain phosphorylation regulates the motility of MDA-MB-231 carcinoma cells. Molecular biology of the cell 18, 3144 (August, 2007).
8. J. W. Shin et al., Contractile forces sustain and polarize hematopoiesis from stem and progenitor cells. Cell stem cell 14, 81 (Jan. 2, 2014).
9. A. F. Straight et al., Dissecting temporal and spatial control of cytokinesis with a myosin II Inhibitor. Science 299, 1743 (Mar. 14, 2003).
10. E. Dona et al., Directional tissue migration through a self-generated chemokine gradient. Nature 503, 285 (Nov. 14, 2013).
11. D. E. Discher, P. Janmey, Y. L. Wang, Tissue cells feel and respond to the stiffness of their substrate. Science 310, 1139 (Nov. 18, 2005).
12. Z. Liu et al., Mechanical tugging force regulates the size of cell-cell junctions. Proceedings of the National Academy of Sciences of the United States of America 107, 9944 (Jun. 1, 2010).
13. H. Y. Yoshikawa et al., Quantitative evaluation of mechanosensing of cells on dynamically tunable hydrogels. Journal of the American Chemical Society 133, 1367 (Feb. 9, 2011).
14. M. Takeichi, Self-organization of animal tissues: cadherin-mediated processes. Developmental cell 21, 24 (Jul. 19, 2011).
15. Y. Sasai, Cytosystems dynamics in self-organization of tissue architecture. Nature 493, 318 (Jan. 17, 2013).

Materials and Methods

Preparation of Mesenchymal Cells (MCs)

As for MCs, any of the following cells was used: cells isolated from human bone marrow, cells isolated from umbilical cord stroma (Wharton's sheath), cells isolated from human auricle, cells isolated from mouse bone marrow, human fibroblast cells or the like. The mesenchymal stem cells isolated from human bone marrow (hMSCs) that were mainly used in this experiment had been cultured using MSCGM™ BulletKit™ (Lonza PT-3001), a medium prepared exclusively for hMSC culture.

Preparation of Various Cells

After anesthetization with diethyl ether (Wako), the abdomens of C57BL/6-Tg (CAG-EGFP) mice (Nippon SLC) at days 12-17 of gestation were disinfected with 70% ethanol and incised to remove embryos. Brain, heart, lung, liver, metanephros or intestine was removed from the embryos. Brain, heart, lung, liver, kidney or intestine was also removed from C57BL/6-BALB/c RFP hairy mice 6 or more weeks of age (purchased from Anticancer Inc.). When cells isolated from these removed tissues were used, they were put in 200 μl of 0.05% Tryspin-EDTA (GIBCO) and incubated for 20 min at 37° C. Subsequently, the tissues were disrupted with a pipette and added to 4.8 ml of a medium. After centrifugation, medium was added and the number of cells was counted. Then, enzyme treatment was conducted to give single cells, which were subsequently used for coculture. When the removed tissues were to be used in a state of small tissues, the removed embryonic tissues were minced with scissors, put in 10 ml of 0.05% Tryspin-EDTA and shaken for 20 min at 37° C. After addition of medium, the resultant cells were passed through a 100 μm cell strainer and centrifuged. After centrifugation, medium was added for use in cell culture. The brain, heart, lung and kidney of the adult mice were minced with scissors and passed through a 100 μm cell strainer. The resultant flow-through was filtered with a 40 μm cell strainer. The cell mass remaining on this cell strainer was collected with medium for use in coculture of cells. With respect to the small intestine of adult mice, the contents were washed with physiological saline. The washed small intestine was cut lengthwise at intervals of 4 cm. The resultant sections were put in 2 mM EDTA, 0.5 mM DTT in PBS and shaken for 20 min at 37° C. Subsequently, the cells were passed through a 100 μm cell strainer, followed by addition of PBS. After centrifugation, the supernatant was suctioned and PBS was added for washing. Then the cells were centrifuged, and medium was added for use in cell culture.

With respect to normal umbilical vein endothelial cells (HUVECs), either cells isolated from the umbilical cords provided by maternal women at the time of delivery after informed consent or purchased cells were cultured in EGM™ BulletKit™ (Lonza CC-4133) through no more than 5 passages. Either type of the cells were fluorescence-labeled with retrovirus vector when necessary. HepG2 was cultured in DMEM supplemented with 10% FBS. Each type of cells were cultured in a 37° C., 5% C02 incubator.

Preparation of Cell Condensates for Self-Organization

On each well of a 24-well plate on which PA gel planar substrate was placed or to which Matrigel coating [Matrigel (BD) either in stock solution or as a mixture with medium at 1:1 was poured at 300 μl/well and left to stand in a 37° C., 5% CO2 incubator for 10 min until it solidified] was applied, $2\times10^6$ cells or more of multiple types in any combination (tissues isolated from embryo or adult, or KO-HepG2, HUVEC, etc.) as mixed with $2\times10^5$ MSCs were seeded. In order to form small-sized cell condensates, $4\times10^3$ cells or more of multiple types in any combination (tissues isolated from embryo or adult, or KO-HepG2, HUVEC) were mixed with $5\times10^3$ or more MSCs and seeded. In either case, the cells were subsequently cultured in a 37° C. incubator for a day. After seeding, chronological observation of cell coculture was performed with a stereomicroscope or a confocal microscope. There is no limitation of the cell types in "any combination". For example, cells derived from different tissues such as pancreas, liver, intestine, nerve, etc. may be mixed and used. Subsequently, an optimal composition for self-organization of an organ of interest could be used.

In experiments performing cell image analyses using plates on which PA gel planar substrate was placed, evaluation was made based on movies of the process of condensate formation as realized by seeding the two types of cells, HUVEC ($2\text{-}4\times10^6$ cells) and hMSC ($2\text{-}4\times10^5$ cells).

Preparation of PA Gel Planar Substrate (Uniform In-Plane Stiffness)

As a gel reaction solution, a 10 ml solution was prepared by mixing aqueous acrylamide solution (40% w/v, A4058, Sigma), aqueous bis-acrylamide solution (2% w/v, M1533, Sigma) and distilled water. In the process, the Young's modulus of the gel was adjusted by changing the mixing ratio of the individual solutions. The resultant reaction solution was bumped using a vacuum chamber. Then, 100 μl of APS (5 g/DW 50 ml, 01307-00, KANTO, 0.20 mm filtered) and 10 μl of TEMED (T9281, Sigma) were sequentially added to the reaction solution. Subsequently, the reaction solution (25 μl) was dripped onto a hydrophobic glass slide (S2112, MATSUNAMI) functionalized with dichlorodimethylsilane (DCDMS, D0358, TCI) and then a round glass coverslip (φ=12-25 mm, MATSUNAMI) treated with allytricholorosilane (ATCS, 107778-5g, Sigma) was placed on top to provide a sandwich structure, which was then left to stand for 30 min. Subsequently, distilled water was added to the sandwiched sample, which was then left to stand overnight. Then, the glass coverslip was peeled off from the glass slide, leaving a gel coat on the former. Phosphate buffer was added to the resultant glass coverslip, which was then left to stand for one day to remove the unreacted monomers. Table 1 below shows representative mixing ratios for the reaction solution and the Young's moduli of gels. The Young's moduli of gels were determined by nanoindentation measurements performed with an atomic force microscope (Nanowizard 3, JPK Instruments, Germany).

Coating of adhesion molecules (Matrigel or laminin) onto the PA gel surface was performed by the procedures described below. First, 0.2 mg/ml N-sulfosuccinimidyl-6-(4'-azido-2'-nitrophenylamino)hexanoate (Sulfo-SANPAH, 22589, Pierce) in 20 mM HEPES (pH 8.5) was dripped onto the PA gel substrate, followed by irradiation with a UV lamp (Z169633-1EA, Sigma) for 20 min. Subsequently, 4.4 mg/ml Matrigel solution [stock solution diluted 227-fold in 20 mM HEPES (pH 8.5), 354234, BD] or 10.0 mg/ml laminin solution [stock solution diluted 227-fold in 20 mM HEPES (pH 8.5), 354232, BD] was dripped in several milliliters onto the gel surface. The resultant gel was left to stand in a 37° C. incubator for 16 hr. Finally, the PA gel was thoroughly rinsed with phosphate buffer to remove the uncrosslinked Matrigel or laminin.

TABLE 1

| Mixing Ratio for Solution and Young's Modulus in Representative Cases of Gel Synthesis | | | | |
|---|---|---|---|---|
| Sample ID | Acrylamide 40% sol [mL] | Bis-acrylamide 2% sol [mL] | Distilled Water [mL] | Young's modulus [kPa] |
| S1 | 0.75 | 0.5 | 8.75 | 1.5 ± 0.1 |
| S2 | 1.25 | 0.75 | 8 | 13.6 ± 1.2 |
| S3 | 1.25 | 1.125 | 7.625 | 17.0 ± 0.3 |
| S4 | 2 | 1.32 | 6.68 | 54.3 ± 1.2 |
| S5 | 2 | 2.4 | 5.6 | 105 ± 33.7 |

Example 2

On each well of a 24-well plate to which Matrigel coating [Matrigel (BD) either in stock solution or as a mixture with medium at 1:1 was poured at 300 μl/well and left to stand in a 37° C., 5% $CO_2$ incubator for 10 min until it solidified] was applied, $2\times10^6$ iPS cell-derived hepatic endoderm cells or human adult hepatocytes as mixed with $5\times10^5$ human or mouse MSCs were seeded. In either case, the cells were subsequently cultured in a 37° C. incubator for a day. After seeding, chronological observation of cell coculture was performed with a stereomicroscope or a confocal microscope. As shown in FIG. 13, even in the absence of vascular endothelial cells, cell condensates could be formed as long as mesenchymal cells were present.

Example 3 Preparation of U-Bottom PA Gel

As a gel reaction solution, a 10 ml solution was prepared by mixing aqueous acrylamide solution (40% w/v, A4058, Sigma), aqueous bis-acrylamide solution (2% w/v, M1533, Sigma) and distilled water. In the process, the Young's modulus of the gel was adjusted by changing the mixing ratio of the individual solutions. This reaction solution (500 μl) was added to a 24-well tissue culture plate (353047, BD). Then, 0.5 μl of TEMED (T9281, Sigma) and 5 μl of APS (5 g/DW 50 ml, 01307-00, KANTO, 0.20 mm filtered) were added to the reaction solution in this order, immediately followed by thorough mixing. Then, the plate was left to stand on a 50° C. hot plate for 15 min. Phosphate buffer was then added and the plate was left to stand for one day to remove the unreacted monomers. A cross section of the resultant U-bottom gel is shown in FIG. 12.

In cell condensate formation experiments using this gel (having a constant stiffness of about 30 kPa at depths of 3 microns and more), $2\times10^6$ iPS cell-derived hepatic endoderm cells, $7\times10^5$ HUVECs and $2\times10^5$ human MSCs were mixed and seeded on each well of 24-well plate. Then, the cells were incubated in a 37° C. incubator for one day. After seeding, chronological observation of cell coculture was performed with a stereomicroscope or a confocal microscope. The results revealed that cell condensates were formed (FIG. 14).

Example 4 Methods and Results

After anesthetization with diethyl ether (Wako), the abdomens of C57BL/6-Tg (CAG-EGFP) mice (Nippon SLC) at days 12.5 and 13.5 of gestation were disinfected with 70% ethanol and incised to remove embryos. Metanephros was removed from the embryos, put in 200 μl of 0.05% Tryspin-EDTA (GIBCO) and incubated for 20 min at 37° C. Subsequently, the tissues were disrupted with a pipette and added to 4.8 ml of a medium. After centrifugation, medium was added and the number of cells was counted. Then, enzyme treatment was conducted to give single cells, which were subsequently used for coculture. Thereafter, the cells were mixed with mesenchymal stem cells isolated from human bone marrow (hMSCs) and normal umbilical vein endothelial cells (HUVECs) and seeded on wells where a solution obtained by mixing Matrigel (the stock solution of Matrigel (BD) used in Example 2) and a medium for vascular endothelial cells (EGM BulletKit™, Lonza CC-4133) at 1:1 had been solidified. In the case of a 24-well plate, cells in any types of combinations were seeded in each well for a total cell count of about $2\times10^6$. The mixing ratio of embryonic renal cells, MSCs and HUVECs was 10:2:0.1-1 but this is not the sole case of the applicable mixing ratio. Thereafter, the cells were cultured in a 37° C. incubator for one day. As a result, three-dimensional tissues formed autonomously. The result shown in the lower left panel of FIG. 16 were obtained from tissues formed by pellet culture. To prepare pellet tissues, the method described in Christodoulos Xinaris et al. (In Vivo Maturation of Functional Renal Organoids Formed from Embryonic Cell Suspensions. J Am Soc Nephrol. 2012 November; 23(11): 1857-1868) was essentially adopted using a technique in which isolated cells as collected simultaneously were allowed to assemble in the bottom of a tube by centrifugal force to form tissues for transplantation.

The renal primordium formed was transplanted into the wombs of immunodeficiency mice. As a result of macroscopic observation, blood perfusion was recognized in two to three days after transplantation (FIG. 15, upper row). The white dotted lines in FIG. 15 indicate the transplantation areas. Scattered cells formed spherical, glomerular tissues at day 8 of transplantation (FIG. 15, bottom row). The results of fluorescence observation as shown in the left panel of FIG. 16 revealed that a great number of glomerular structures were formed by culturing on a support but that this was not the case when the conventional method (pellet transplantation group) was applied. The results of comprehensive gene expression analyses as shown in FIG. 16, right panel, revealed that the transplants at one month after transplantation had matured to a degree equivalent to that of 0-8 weeks after birth. As shown in the three left columns of FIG. 17, the results of electron microscopy targeting tissues at week 4 of transplantation revealed that the resulting tissues formed normal nephron structures comprising podocytes, slit membranes, endothelial cells, proximal tubules, mesangial cells and the like. As shown in the rightmost panel of FIG. 17, the results of immunostaining confirmed the presence of podocytes and slit membranes. Further, the results of fluorescence live observation as performed after administration of low molecular weight fluorescence dextran at week 3 of transplantation are also shown (FIG. 18). The tissues formed first flowed into blood vessels, were filtered inside glomeruli, and collected in proximal tubules, indicating that they had the primitive urine producing function of the kidney (FIG. 18). As described above, by transplanting into a living body the renal primordium artificially prepared according to the present invention, autonomous maturation could successfully be induced to prepare functional renal tissues.

Example 5 Methods and Results

Changes in the Young's Modulus of supports (see "preparation of PA gel planar substrate") with different stiffness conditions (Samples A, B and C) before (oblique lines) and after (solid black) Matrigel coating. It was shown that the stiffness conditions can be strictly controlled regardless of the presence or absence of the coating (FIG. 19). The gel substrate used in Example 5 was prepared according to the method described in Example 1.

Example 6 Methods and Results

Gels having multiple stiffness patterns providing different stiffness conditions could successfully be prepared on one substrate (FIG. 20). According to pattern 1, a gel with a hard central part was prepared and according to pattern 2, a gel with a less hard central part was prepared (FIG. 20, left panel). The right panel of FIG. 20 shows the results of measurement of stiffness conditions along the major axis, indicating that the intended stiffness conditions could be achieved.

Gel substrates having spatial patterns of stiffness were prepared by the method described below. As a gel reaction solution, a 10 ml solution was prepared by mixing aqueous acrylamide solution (40% w/v, A4058, Sigma), aqueous bis-acrylamide solution (2% w/v, M1533, Sigma) and distilled water. Subsequently, with light shielded, 50 mg of Irgacure 2959 (0.5% w/v, DY15444, Ciba) was added and dissolved in a hot water bath at 37° C. The resultant reaction solution was bumped in a vacuum chamber. Then, 10 μl of this reaction solution was dripped onto a hydrophobic glass slide (S2112, MATSUNAMI) functionalized with dichlorodimethylsilane (DCDMS, D0358, TCI) and then a round glass coverslip (φ=12 mm, MATSUNAMI) treated with allytricholorosilane (ATCS, 107778-5g, Sigma) was placed on top to provide a sandwich structure. A photomask was placed on the sandwiched sample and irradiated with UV light at 254 nm. The photomask was made from acetyl cellulose (G254B, Agar) by printing with a laser printer (MC860, OKI). Using Adobe Photoshop as a mask pattern designer, a circular mask (12 mm o.d. and 2-4 mm i.d.) was prepared. For irradiation, a mercury lamp (C-HGFI, Nikon) was used as a light source and fiber optics was combined with a light projection tube to ensure uniform irradiation of the reaction solution. The time of UV irradiation was adjusted by minutes depending on the desired stiffness. Subsequently, distilled water was added to the sandwiched sample and the glass coverslip was peeled off from the glass slide, leaving a gel coat on the former. Phosphate buffer was added to the resultant glass coverslip, which was then left to stand for one day to remove the unreacted monomers. The Young's moduli of gels were determined by nanoindentation measurements performed with an atomic force microscope (Nanowizard 3, JPK Instruments, Germany). Coating of adhesion molecules (Matrigel or laminin) onto the PA gel surface was performed by the procedures described below. First, 0.2 mg/ml N-sulfosuccinimidyl-6-(4'-azido-2'-nitrophenylamino)hexanoate (Sulfo-SANPAH, 22589, Pierce) in 20 mM HEPES (pH 8.5) was dripped onto the PA gel substrate, followed by irradiation with a UV lamp (Z169633-1EA, Sigma) for 20 mM. Subsequently, 1 ml of 4.4 mg/ml Matrigel solution [stock solution diluted 227-fold in 20 mM HEPES (pH 8.5), 354234, BD] or 10.0 mg/ml laminin solution [stock solution diluted 227-fold in 20 mM HEPES (pH 8.5), 354232, BD] was dripped in one milliliter onto the gel surface. The resultant gel was left to stand in a 37° C. incubator for 16 hr. Finally, the PA gel was thoroughly rinsed with phosphate buffer to remove the uncross-linked Matrigel or laminin.

Subsequently, iPS cell-derived hepatic endoderm cells, HUVECs and MSCs were mixed at a ratio of 10:7:2 and the mixture was seeded on the patterned gels to give a total cell count of about $2\times10^6$ cells (FIG. 21). As a result, in the gel with pattern 1, cells gathered in the central hard area within 30 hr after seeding to rapidly form condensates in the gel with pattern 2, formation of condensates was recognized but the velocity of cell movement toward the central part was slightly delayed. It was therefore suggested that the optimal condition for the stiffness of the central part was 100 kPa.

Example 7 Methods and Results

A positive pattern was so designed that individual circular parts were hard and their periphery was soft (FIG. 22, left panel). A negative pattern was so designed that individual circular parts were soft and their periphery was hard (FIG. 22, right panel). Gel substrates with such multiple patterns of stiffness were prepared based on the technique described in Example 6 and by exposing a gel substrate (25 mm in diameter) through a photomask with a 4×4 pattern of circles (diameter: about 2 mm; center-to-center distance between circles: about 2.7 mm). It is believed that by using these patterned supports, cell condensates of any size may be formed at any place.

All publications, patents and patent applications cited herein are incorporated herein by reference in their entirety.

The invention claimed is:

1. A method of preparing a cell condensate in vitro, comprising culturing a mixture of cells and/or tissues of a desired type and mesenchymal cells to form a cell condensate, wherein the culture is performed on a U- or V-shaped bottom support, wherein the support comprises a gel-like support on which the mesenchymal cell is capable of contraction, wherein a size of the cell condensate is 1 mm or more, the cells mixed with the mesenchymal cells are pluripotent cells, and/or the tissues mixed with the mesenchymal cells are tissues induced from pluripotent cells, and wherein stiffness of a central part of the gel-like support is greater than stiffness of a peripheral part thereof, stiffness of a peripheral part of the gel-like support is greater than stiffness of a central part thereof, the gel-like support is patterned and has one or more patterns in which stiffness of a central part is greater than stiffness of a peripheral part, or the gel-like support is patterned and has one or more patterns in which stiffness of a peripheral part is greater than stiffness of a central part.

2. The method of claim 1, wherein the cell condensate is capable of forming a three-dimensional tissue structure that has been provided with higher structures by self-organization.

3. The method of claim 1, wherein the stiffness of a central part of the gel-like support is greater than stiffness of a peripheral part thereof.

4. The method of claim 1, wherein the stiffness of a peripheral part of the gel-like support is greater than stiffness of a central part thereof.

5. The method of claim 1, wherein the gel-like support is patterned and has one or more patterns in which the stiffness of a central part is greater than stiffness of a peripheral part.

6. The method of claim 1, wherein the gel-like support is patterned and has one or more patterns in which the stiffness of a peripheral part is greater than stiffness of a central part.

7. The method of claim 1, wherein a total cell count of the cells and/or tissues of a desired type is 400,000 or more and a total cell count of the mesenchymal cells are 100,000 to 400,000 in number.

8. The method of claim 1, wherein the size of the cell condensate is 1 mm or more.

9. The method of claim 1, wherein the cell condensate is formed autonomously.

10. The method of claim 1, wherein the mixture of cells and/or tissues of a desired type and mesenchymal cells is cultured without using scaffold materials.

11. The method of claim 1, wherein the cells and/or tissues mixed with the mesenchymal cells are derived from liver, pancreas, intestine, lung, kidney, heart, brain or cancer.

12. The method of claim 1, wherein the cells mixed with the mesenchymal cells are pluripotent cells.

13. The method of claim 12, wherein the pluripotent cell is a pluripotent cell obtained from a living body, a pluripotent cell obtained by induction from reprogramming or a mixture thereof.

14. The method of claim 1, wherein the tissues mixed with the mesenchymal cells are tissues induced from pluripotent cells.

15. The method of claim 1, wherein said mixture of cells and/or tissues of a desired type and mesenchymal cells is only cells cultured in the method.

16. The method of claim 1, wherein the mesenchymal cells form support structures for the cells of a desired type in the cell condensate.

17. The method of claim 1, herein the gel support has a stiffness from 10 KPa to 18 Kpa.

18. A method of preparing a cell condensate in vitro, comprising culturing a mixture of cells and/or tissues of a desired type and mesenchymal cells to form a cell condensate, in which the mesenchymal cells exclude fibroblast, wherein the culture is performed on a U- or V-shaped bottom support, wherein the support comprises a gel-like support on which the mesenchymal cell is capable of contraction, wherein a total cell count of the cells and/or tissues of a desired type is 400,000 or more and a total cell count of the mesenchymal cells are 100,000 to 400,000 in number, or the cells and/or tissues mixed with the mesenchymal cells are derived from liver, pancreas, intestine, lung, kidney, heart, brain or cancer, and wherein stiffness of a central part of the gel-like support is greater than stiffness of a peripheral part thereof, stiffness of a peripheral part of the gel-like support is greater than stiffness of a central part thereof, the gel-like support is patterned and has one or more patterns in which stiffness of a central part is greater than stiffness of a peripheral part, or the gel-like support is patterned and has one or more patterns in which stiffness of a peripheral part is greater than stiffness of a central part.

* * * * *